US009267119B2

(12) United States Patent
Anderson et al.

(10) Patent No.: US 9,267,119 B2
(45) Date of Patent: Feb. 23, 2016

(54) PHOSPHATIDYLINOSITOL PHOSPHATE KINASE TYPE 1 GAMMA SPLICE VARIANTS AS BIOMARKERS AND DRUG TARGETS FOR EPITHELIAL CANCERS

(71) Applicant: WISCONSIN ALUMNI RESEARCH FOUNDATION, Madison, WI (US)

(72) Inventors: Richard A. Anderson, Cross Plains, WI (US); Nicholas J. Schill, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 340 days.

(21) Appl. No.: 13/690,903

(22) Filed: Nov. 30, 2012

(65) Prior Publication Data

US 2013/0157268 A1 Jun. 20, 2013

Related U.S. Application Data

(62) Division of application No. 12/243,664, filed on Oct. 1, 2008, now Pat. No. 8,357,790.

(60) Provisional application No. 60/976,928, filed on Oct. 2, 2007.

(51) Int. Cl.

| | |
|---|---|
| ***C12N 9/12*** | (2006.01) |
| ***C12Q 1/48*** | (2006.01) |
| ***C12Q 1/68*** | (2006.01) |
| ***G01N 33/574*** | (2006.01) |

(52) U.S. Cl.

CPC ............ *C12N 9/1229* (2013.01); *C12N 9/1205* (2013.01); *C12Q 1/485* (2013.01); *C12Q 1/6886* (2013.01); *G01N 33/57415* (2013.01); *C12Q 2600/118* (2013.01); *C12Q 2600/136* (2013.01); *C12Q 2600/158* (2013.01); *G01N 2500/00* (2013.01)

(58) Field of Classification Search

None

See application file for complete search history.

(56) References Cited

U.S. PATENT DOCUMENTS

| | | | |
|---|---|---|---|
| 6,893,834 | B2 | 5/2005 | Goueli et al. |
| 2009/0208949 | A1 | 8/2009 | Anderson et al. |

OTHER PUBLICATIONS

Di Paolo et al. (Nature, 2002, vol. 420, p. 85-89).*

6th Annual MCP Research Training Symposium, University of Wisconsin—Madison, Oct. 3, 2006, Select Abstracts, 6 pages.

James et al. "Genomic Libraries and a Host Strain Designed for Highly Efficient Two-Hybrid Selection in Yeast," Genetics, 1996, vol. 144, No. 4, pp. 1425-1436.

Lee et al., "Regulation of the Interaction between PIPKI-gamma and Talin by Proline-Directed Protein Kinases," J. Cell Biol., 2005, vol. 168, No. 5, pp. 789-799.

Ling et al. "Type I-gamma Phosphatidylinositol phosphate kinase targets and regulates focal adhesions," Nature, Nov. 7, 2002, vol. 420, pp. 89-93.

Ling et al., "Movin' on up: the role of Ptdlns (4,5)P2 in cell migration," TRENDS in Cell Biology, Jun. 2006, vol. 16, No. 6, pp. 276-284.

Ling et al., "Type I Gamma Phosphatidylinositol Phosphate Kinase Targets and Regulates Focal Adhesions," Nature, 2002, vol. 420, No. 6911, pp. 89-93.

Non-final Office Action received for U.S. Appl. No. 12/243,664 dated Dec. 12, 2011.

Notice of Allowance mailed on Aug. 16, 2012 for U.S. Appl. No. 12/243,664 (including Examiner-initiated interview summary), 10 pp.

Schill et al., "Interacting Partners Confer Specific Functions to PIPKI Splice Variants," Poster as Presented at the University of Wisconsin, Madison, Wisconsin Signal Transduction Symposium on Oct. 3, 2006 (7 pgs.).

Sun et al., "Type I Gamma Phosphatidylinositol Phosphate Kinase is Required for EGF-Stimulated Directional Cell Migration," J. Cell Biol., 2007, vol. 178, pp. 297-308.

Towler et al., Clathrin Isoform CHC22, a Component of Neuromuscular and Myotendinous Junctions, Binds Sorting Nexin 5 and Has Increased Expression During Myogenesis and Muscle Regeneration, Mol Bio Cell, 2004, vol. 15, Issue 7, pp. 3181-3195.

* cited by examiner

*Primary Examiner* — Stephanie K Mummert

(74) *Attorney, Agent, or Firm* — Foley & Lardner LLP

(57) ABSTRACT

The present invention relates generally to the field of phosphatidylinositol based signaling pathways, and more specifically to the use of novel members of these pathways for disease prognosis and treatment. In some aspects, the present invention relates to the use of novel splice variants of type I phosphatidylinositol phosphate kinase γ, named PIPKIγ 700 and PIPKIγ 707, to determine breast cancer and breast cancer prognosis.

5 Claims, 34 Drawing Sheets

FIGURE 13

| Biomarkers | Correlations/Spearman's rho | PIPKIγ positive | PIPKIγ negative |
|---|---|---|---|
| PIPKIγ positive | Correlation Coefficient | 1 | -0.286 |
| | Sig. (2-tailed) | | 0.000001 |
| | N | 438 | 438 |
| PIPKIγ negative | Correlation Coefficient | -0.286** | 1 |
| | Sig. (2-tailed) | 0.000001 | |
| | N | 438 | 438 |
| E-cadherin positive | Correlation Coefficient | 0.199692786 | -0.117721982 |
| | Sig. (2-tailed) | 0.000026 | 0.013690781 |
| | N | 438 | 438 |
| E-cadherin negative | Correlation Coefficient | -0.098237626 | 0.274531841 |
| | Sig. (2-tailed) | 0.039873291 | 0.000001 |
| | N | 438 | 438 |
| HER1 | Correlation Coefficient | 0.242 | -0.131 |
| | Sig. (2-tailed) | 0.000005 | 0.015 |
| | N | 346 | 346 |
| HER2 | Correlation Coefficient | 0.164 | -0.102 |
| | Sig. (2-tailed) | 0.0026 | 0.062 |
| | N | 337 | 337 |
| HER1 or HER2 | Correlation Coefficient | 0.291 | -0.185 |
| | Sig. (2-tailed) | 0.000001 | 0.001 |
| | N | 299 | 299 |
| HER3 | Correlation Coefficient | -0.041 | -0.055 |
| | Sig. (2-tailed) | 0.496 | 0.365 |
| | N | 278 | 278 |
| HER3_01 | Correlation Coefficient | -0.013 | -0.069 |
| | Sig. (2-tailed) | 0.835 | 0.253 |
| | N | 278 | 278 |
| ER | Correlation Coefficient | -0.327 | 0.179 |
| | Sig. (2-tailed) | 0.000001 | 0.0015 |
| | N | 324 | 324 |
| p53 | Correlation Coefficient | 0.269 | -0.135 |
| | Sig. (2-tailed) | 0.000002 | 0.0178 |
| | N | 309 | 309 |

**. Correlation is significant at the .01 level (2-tailed).

FIGURE 21

SEQ ID NO: 1 PIPKIγ 700 DNA

5'ATGGAGCTGGAGGTACCGGACGAGGCGGAGAGCGCTGAGGCGGGGGCCGT
GCCCTCGGAGGCGGCGTGGGCGGCAGAGAGCGGGGCGGCGGCAGGTTTGGC
TCAGAAGAAGGCGGCCCCAACAGAGGTTCTGTCCATGACGGCACAGCCGGG
CCCTGGCCATGGGAAGAAGTTGGGCCATCGAGGTGTGGACGCATCCGGCGAA
ACCACCTACAAGAAGACCACCTCCTCCACCCTGAAGGGTGCCATCCAGCTGG
GCATCGGCTACACCGTGGGCCACCTGAGCTCCAAGCCCGAACGCGACGTGCT
CATGCAGGACTTCTACGTGGTGGAGAGCATCTTCTTCCCCAGCGAAGGCAGC
AACCTCACCCCCGCCCACCACTTCCAGGACTTCCGCTTCAAGACCTATGCACC
TGTCGCCTTCCGCTACTTCCGGGAGCTCTTTGGGATCCGGCCAGATGATTACT
TGTACTCCCTGTGCAATGAGCCGCTGATCGAGCTGTCCAACCCGGGCGCCAG
TGGCTCCCTCTTCTACGTCACCAGCGACGACGAGTTCATCATCAAGACCGTCA
TGCACAAGGAGGCCGAGTTCCTGCAGAAGCTGCTCCCTGGCTACTACATGAA
CCTCAACCAGAACCCGCGGACGCTGCTGCCCAAGTTCTATGGGCTGTACTGC
GTGCAGTCGGGGGGCAAGAACATCCGCGTCGTGGTCATGAACAACATCCTGC
CCCGCGTGGTCAAGATGCACCTCAAGTTCGACCTCAAGGGCTCCACCTACAA
GCGGCGCGCCAGCAAGAAGGAGAAGGAGAAGAGCTTCCCCACCTACAAGGA
CCTGGACTTCATGCAGGACATGCCCGAGGGGCTCCTGCTGGACGCCGACACC
TTCAGCGCCCTGGTCAAGACGCTGCAGCGGGACTGCCTGGTCCTGGAAAGTT
TCAAGATCATGGACTACAGCCTGCTGCTGGGCGTGCACAACATCGACCAGCA
CGAGCGCGAGCGGCAGGCGCAGGGCGCCCAGAGCACCTCAGATGAGAAGCG
GCCTGTGGGCCAGAAGGCGCTCTACTCCACGGCCATGGAGTCCATCCAGGGT
GGCGCCGCGCGCGGGGAGGCCATCGAATCGGATGACACGATGGGCGGGATC
CCCGCTGTGAACGGCCGCGGGGAGCGGCTGCTGCTGCACATTGGCATCATCG
ACATCCTGCAGTCCTACAGGTTCATCAAGAAACTGGAGCACACCTGGAAGGC
CCTCGTCCACGATGGGGACACGGTGTCCGTCCACCGCCCCAGCTTCTATGCCG

FIGURE 21 (cont.)

AGCGCTTTTTCAAGTTCATGAGCAACACGGTCTTTCGGAAGAACTCCTCCCTG
AAGTCCTCGCCCTCCAAGAAGGGGCGCGGCGGAGCCTTGCTAGCTGTGAAAC
CGCTGGGGCCCACCGCTGCCTTCTCGGCCAGCCAGATCCCTAGCGAGCGGGA
GGAGGCCCAGTACGACCTGCGGGGGGCCCGCAGCTACCCCACGCTGGAGGA
CGAAGGCCGGCCCGACCTCCTGCCCTGCACGCCACCTTCTTTCGAAGAAGCC
ACTACAGCCTCCATTGCCACGACTCTGTCATCCACATCCCTCTCCATTCCTGA
GCGGTCCCCCTCGGAGACGTCGGAGCAGCCGCGGTACAGGCGGCGCACACA
GTCGTCTGGACAGGATGGCAGGCCGCAGGAGGAGCCACCCGCGGAAGAGGA
TCTGCAGCAGATTACAGTGCAGGTGGAGCCTGCGTGCAGCGTGGAGATTGTG
GTCCCCAAAGAGGAGGACGCAGGGGTGGAGGCTTCCCCGGCCGGTGCCTCTG
CTGCTGTTGAAGTAGAAACTGCCAGCCAGGCCTCAGACGAGGAGGGCGCACC
TGCCAGCCAGGCCTCGGACGAGGAGGACGCGCCCGCCACCGACATCTACTTT
TGGCGCCTCTGGGGTCCCCATGCACCCACCTGGCCCTGGAGAAGGGAGGGAC
GGGCCGCGTGCCTGTGCCCCTACCCACCGCACGTCGTCACCCCTTTTCCTGGG
ACTGGTTTGTGCGCGTCCTGGTCTCCGGATGGTACGGGGGGCCTGGGGGCCA
TGTCGTGCTGTGTGTCTGTGTCCTGA-3’

FIGURE 22

SEQ ID NO: 2 PIPKIγ 707 DNA

5’ATGGAGCTGGAGGTACCGGACGAGGCGGAGAGCGCTGAGGCGGGGGCCGT
GCCCTCGGAGGCGGCGTGGGCGGCAGAGAGCGGGGCGGCGGCAGGTTTGGC
TCAGAAGAAGGCGGCCCCAACAGAGGTTCTGTCCATGACGGCACAGCCGGG
CCCTGGCCATGGGAAGAAGTTGGGCCATCGAGGTGTGGACGCATCCGGCGAA
ACCACCTACAAGAAGACCACCTCCTCCACCCTGAAGGGTGCCATCCAGCTGG
GCATCGGCTACACCGTGGGCCACCTGAGCTCCAAGCCCGAACGCGACGTGCT
CATGCAGGACTTCTACGTGGTGGAGAGCATCTTCTTCCCCAGCGAAGGCAGC
AACCTCACCCCCGCCCACCACTTCCAGGACTTCCGCTTCAAGACCTATGCACC
TGTCGCCTTCCGCTACTTCCGGGAGCTCTTTGGGATCCGGCCAGATGATTACT
TGTACTCCCTGTGCAATGAGCCGCTGATCGAGCTGTCCAACCCGGGCGCCAG
TGGCTCCCTCTTCTACGTCACCAGCGACGACGAGTTCATCATCAAGACCGTCA
TGCACAAGGAGGCCGAGTTCCTGCAGAAGCTGCTCCCTGGCTACTACATGAA
CCTCAACCAGAACCCGCGGACGCTGCTGCCCAAGTTCTATGGGCTGTACTGC
GTGCAGTCGGGGGGCAAGAACATCCGCGTCGTGGTCATGAACAACATCCTGC
CCCGCGTGGTCAAGATGCACCTCAAGTTCGACCTCAAGGGCTCCACCTACAA
GCGGCGCGCCAGCAAGAAGGAGAAGGAGAAGAGCTTCCCCACCTACAAGGA
CCTGGACTTCATGCAGGACATGCCCGAGGGGCTCCTGCTGGACGCCGACACC
TTCAGCGCCCTGGTCAAGACGCTGCAGCGGGACTGCCTGGTCCTGGAAAGTT
TCAAGATCATGGACTACAGCCTGCTGCTGGGCGTGCACAACATCGACCAGCA
CGAGCGCGAGCGGCAGGCGCAGGGCGCCCAGAGCACCTCAGATGAGAAGCG
GCCTGTGGGCCAGAAGGCGCTCTACTCCACGGCCATGGAGTCCATCCAGGGT
GGCGCCGCGCGCGGGGAGGCCATCGAATCGGATGACACGATGGGCGGGATC
CCCGCTGTGAACGGCCGCGGGGAGCGGCTGCTGCTGCACATTGGCATCATCG
ACATCCTGCAGTCCTACAGGTTCATCAAGAAACTGGAGCACACCTGGAAGGC
CCTCGTCCACGATGGGGACACGGTGTCCGTCCACCGCCCCAGCTTCTATGCCG

FIGURE 22 (cont.)

AGCGCTTTTTCAAGTTCATGAGCAACACGGTCTTTCGGAAGAACTCCTCCCTG
AAGTCCTCGCCCTCCAAGAAGGGGCGCGGCGGAGCCTTGCTAGCTGTGAAAC
CGCTGGGGCCCACCGCTGCCTTCTCGGCCAGCCAGATCCCTAGCGAGCGGGA
GGAGGCCCAGTACGACCTGCGGGGGGCCCGCAGCTACCCCACGCTGGAGGA
CGAAGGCCGGCCCGACCTCCTGCCCTGCACGCCACCTTCTTTCGAAGAAGCC
ACTACAGCCTCCATTGCCACGACTCTGTCATCCACATCCCTCTCCATTCCTGA
GCGGTCCCCCTCGGAGACGTCGGAGCAGCCGCGGTACAGGCGGCGCACACA
GTCGTCTGGACAGGATGGCAGGCCGCAGGAGGAGCCACCCGCGGAAGAGGA
TCTGCAGCAGATTACAGTGCAGGTGGAGCCTGCGTGCAGCGTGGAGATTGTG
GTCCCCAAAGAGGAGGACGCAGGGGTGGAGGCTTCCCCGGCCGGTGCCTCTG
CTGCTGTTGAAGTAGAAACTGCCAGCCAGGCCTCAGACGAGGAGGGCGCACC
TGCCAGCCAGGCCTCGGACGAGGAGGACGCGCCCGCCACCGACATCTACTTT
TTCACGGATGGGAGGTACTGGATTTACTCTCCCCGCCATCGCCGACTGCGGG
CCGTGACGCTGAGCGCCTCGGGGACTGTAAGTGACCGCAGCCGGCCACCCTG
GGGAGAAGGGGCAGTGCCCCTCGGGCAGCAGGGAGCCGCAGGTCCCCGGCC
GGAAGCTCAGTGTCTGACGTCAGTTGTTTTCCAGAAGGGCTTTGGGTAA-3’

FIGURE 23

SEQ ID NO: 3 700 PROTEIN

MELEVPDEAESAEAGAVPSEAAWAAESGAAAGLAQKKAAPTEVLSMTAQPGPG
HGKKLGHRGVDASGETTYKKTTSSTLKGAIQLGIGYTVGHLSSKPERDVLMQDF
YVVESIFFPSEGSNLTPAHHFQDFRFKTYAPVAFRYFRELFGIRPDDYLYSLCNEP
LIELSNPGASGSLFYVTSDDEFIIKTVMHKEAEFLQKLLPGYYMNLNQNPRTLLPK
FYGLYCVQSGGKNIRVVVMNNILPRVVKMHLKFDLKGSTYKRRASKKEKEKSF
PTYKDLDFMQDMPEGLLLDADTFSALVKTLQRDCLVLESFKIMDYSLLLGVHNI
DQHERERQAQGAQSTSDEKRPVGQKALYSTAMESIQGGAARGEAIESDDTMGGI
PAVNGRGERLLLHIGIIDILQSYRFIKKLEHTWKALVHDGDTVSVHRPSFYAERFF
KFMSNTVFRKNSSLKSSPSKKGRGGALLAVKPLGPTAAFSASQIPSEREEAQYDL
RGARSYPTLEDEGRPDLLPCTPPSFEEATTASIATTLSSTSLSIPERSPSETSEQPRY
RRRTQSSGQDGRPQEEPPAEEDLQQITVQVEPACSVEIVVPKEEDAGVEASPAGA
SAAVEVETASQASDEEGAPASQASDEEDAPATDIYFWRLWGPHAPTWPWRREG
RAACLCPYPPHVVTPFPGTGLCASWSPDGTGGLGAMSCCVSVS

FIGURE 24

SEQ ID NO: 4 707 PROTEIN

MELEVPDEAESAEAGAVPSEAAWAAESGAAAGLAQKKAAPTEVLSMTAQPGPG
HGKKLGHRGVDASGETTYKKTTSSTLKGAIQLGIGYTVGHLSSKPERDVLMQDF
YVVESIFFPSEGSNLTPAHHFQDFRFKTYAPVAFRYFRELFGIRPDDYLYSLCNEP
LIELSNPGASGSLFYVTSDDEFIIKTVMHKEAEFLQKLLPGYYMNLNQNPRTLLPK
FYGLYCVQSGGKNIRVVVMNNILPRVVKMHLKFDLKGSTYKRRASKKEKEKSF
PTYKDLDFMQDMPEGLLLDADTFSALVKTLQRDCLVLESFKIMDYSLLLGVHNI
DQHERERQAQGAQSTSDEKRPVGQKALYSTAMESIQGGAARGEAIESDDTMGGI
PAVNGRGERLLLHIGIIDILQSYRFIKKLEHTWKALVHDGDTVSVHRPSFYAERFF
KFMSNTVFRKNSSLKSSPSKKGRGGALLAVKPLGPTAAFSASQIPSEREEAQYDL
RGARSYPTLEDEGRPDLLPCTPPSFEEATTASIATTLSSTSLSIPERSPSETSEQPRY
RRRTQSSGQDGRPQEEPPAEEDLQQITVQVEPACSVEIVVPKEEDAGVEASPAGA
SAAVEVETASQASDEEGAPASQASDEEDAPATDIYFFTDGRYWIYSPRHRRLRAV
TLSASGTVSDRSRPPWGEGAVPLGQQGAAGPRPEAQCLTSVVFQKGFG

FIGURE 25

SEQ ID NO: 5 700 C-TERM DNA

5'TGGCGCCTCTGGGGTCCCCATGCACCCACCTGGCCCTGGAGAAGGGAGGGA
CGGGCCGCGTGCCTGTGCCCCTACCCACCGCACGTCGTCACCCCTTTTCCTGG
GACTGGTTTGTGCGCGTCCTGGTCTCCGGATGGTACGGGGGGCCTGGGGGCC
ATGTCGTGCTGTGTGTCTGTGTCCTGA-3'

FIGURE 26

SEQ ID NO: 6 700 C-TERM PROTEIN

WRLWGPHAPTWPWRREGRAACLCPYPPHVVTPFPGTGLCASWSPDGTGGLGA
MSCCVSVS

FIGURE 27

SEQ ID NO: 7 707 C-TERM DNA

5'TTCACGGATGGGAGGTACTGGATTTACTCTCCCCGCCATCGCCGACTGCGG
GCCGTGACGCTGAGCGCCTCGGGGACTGTAAGTGACCGCAGCCGGCCACCCT
GGGGAGAAGGGGCAGTGCCCCTCGGGCAGCAGGGAGCCGCAGGTCCCCGGC
CGGAAGCTCAGTGTCTGACGTCAGTTGTTTTCCAGAAGGGCTTTGGGTAA-3'

FIGURE 28

SEQ ID NO: 8 707 C-TERM PROTEIN

FTDGRYWIYSPRHRRLRAVTLSASGTVSDRSRPPWGEGAVPLGQQGAAGPRPEA
QCLTSVVFQKGFG

FIGURE 29

SEQ ID NO: 9 SNX 5 PROTEIN

MAAVPELLQQQEEDRSKLRSVSVDLNVDPSLQIDIPDALSERDKVKFTVHTKTTL
PTFQSPEFSVTRQHEDFVWLHDTLIETTDYAGLIIPPAPTKPDFDGPREKMQKLGE
GEGSMTKEEFAKMKQELEAEYLAVFKKTVSSHEVFLQRLSSHPVLSKDRNFHVF
LEYDQDLSVRRKNTKEMFGGFFKSVVKSADEVLFTGVKEVDDFFEQEKNFLINY
YNRIKDSCVKADKMTRSHKNVADDYIHTAACLHSLALEEPTVIKKYLLKVAELF
EKLRKVEGRVSSDEDLKLTELLRYYMLNIEAAKDLLYRRTKALIDYENSNKALD
KARLKSKDVKLAEAHQQECCQKFEQLSESAKEELINFKRKRVAAFRKNLIEMSE
LEIKHARNNVSLLQSCIDLFKNN

FIGURE 30

SEQ ID NO: 10 LMO4 PROTEIN

MVNPGSSSQPPPVTAGSLSWKRCAGCGGKIADRFLLYAMDSYWHSRCLKCSCC
QAQLGDIGTSCYTKSGMILCRNDYIRLFGNSGACSACGQSIPASELVMRAQGNV
YHLKCFTCSTCRNRLVPGDRFHYINGSLFCEHDRPTALINGHLNSLQSNPLLPDQ
KVC

FIGURE 31

SEQ ID NO: 11 KINASE INACTIVE PIPKIγ700 D316A

MELEVPDEAESAEAGAVPSEAAWAAESGAAAGLAQKKAAPTEVLSMTAQPGPG
HGKKLGHRGVDASGETTYKKTTSSTLKGAIQLGIGYTVGHLSSKPERDVLMQDF
YVVESIFFPSEGSNLTPAHHFQDFRFKTYAPVAFRYFRELFGIRPDDYLYSLCNEP
LIELSNPGASGSLFYVTSDDEFIIKTVMHKEAEFLQKLLPGYYMNLNQNPRTLLPK
FYGLYCVQSGGKNIRVVVMNNILPRVVKMHLKFDLKGSTYKRRASKKEKEKSF
PTYKDLDFMQDMPEGLLLDADTFSALVKTLQRDCLVLESFKIMAYSLLLGVHNI
DQHERERQAQGAQSTSDEKRPVGQKALYSTAMESIQGGAARGEAIESDDTMGGI
PAVNGRGERLLLHIGIIDILQSYRFIKKLEHTWKALVHDGDTVSVHRPSFYAERFF
KFMSNTVFRKNSSLKSSPSKKGRGGALLAVKPLGPTAAFSASQIPSEREEAQYDL
RGARSYPTLEDEGRPDLLPCTPPSFEEATTASIATTLSSTSLSIPERSPSETSEQPRY
RRRTQSSGQDGRPQEEPPAEEDLQQITVQVEPACSVEIVVPKEEDAGVEASPAGA
SAAVEVETASQASDEEGAPASQASDEEDAPATDIYFWRLWGPHAPTWPWRREG
RAACLCPYPPHVVTPFPGTGLCASWSPDGTGGLGAMSCCVSVS

FIGURE 32

SEQ ID NO: 12 KINASE INACTIVE PIPKIγ707 D316A

MELEVPDEAESAEAGAVPSEAAWAAESGAAAGLAQKKAAPTEVLSMTAQPGPG
HGKKLGHRGVDASGETTYKKTTSSTLKGAIQLGIGYTVGHLSSKPERDVLMQDF
YVVESIFFPSEGSNLTPAHHFQDFRFKTYAPVAFRYFRELFGIRPDDYLYSLCNEP
LIELSNPGASGSLFYVTSDDEFIIKTVMHKEAEFLQKLLPGYYMNLNQNPRTLLPK
FYGLYCVQSGGKNIRVVVMNNILPRVVKMHLKFDLKGSTYKRRASKKEKEKSF
PTYKDLDFMQDMPEGLLLDADTFSALVKTLQRDCLVLESFKIMAYSLLLGVHNI
DQHERERQAQGAQSTSDEKRPVGQKALYSTAMESIQGGAARGEAIESDDTMGGI
PAVNGRGERLLLHIGIIDILQSYRFIKKLEHTWKALVHDGDTVSVHRPSFYAERFF
KFMSNTVFRKNSSLKSSPSKKGRGGALLAVKPLGPTAAFSASQIPSEREEAQYDL
RGARSYPTLEDEGRPDLLPCTPPSFEEATTASIATTLSSTSLSIPERSPSETSEQPRY
RRRTQSSGQDGRPQEEPPAEEDLQQITVQVEPACSVEIVVPKEEDAGVEASPAGA
SAAVEVETASQASDEEGAPASQASDEEDAPATDIYFFTDGRYWIYSPRHRRLRAV
TLSASGTVSDRSRPPWGEGAVPLGQQGAAGPRPEAQCLTSVVFQKGFG

SEQUENCE LISTING

```
<160> NUMBER OF SEQ ID NOS: 17

<210> SEQ ID NO 1
<211> LENGTH: 2103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atggagctgg aggtaccgga cgaggcggag agcgctgagg cgggggccgt gccctcggag     60

gcggcgtggg cggcagagag cggggcggcg gcaggtttgg ctcagaagaa ggcggcccca    120

acagaggttc tgtccatgac ggcacagccg ggccctggcc atgggaagaa gttgggccat    180

cgaggtgtgg acgcatccgg cgaaaccacc tacaagaaga ccacctcctc caccctgaag    240

ggtgccatcc agctgggcat cggctacacc gtgggccacc tgagctccaa gcccgaacgc    300

gacgtgctca tgcaggactt ctacgtggtg gagagcatct tcttccccag cgaaggcagc    360

aacctcaccc ccgcccacca cttccaggac ttccgcttca agacctatgc acctgtcgcc    420

ttccgctact tccgggagct ctttgggatc cggccagatg attacttgta ctccctgtgc    480

aatgagccgc tgatcgagct gtccaacccg ggcgccagtg gctccctctt ctacgtcacc    540

agcgacgacg agttcatcat caagaccgtc atgcacaagg aggccgagtt cctgcagaag    600

ctgctccctg gctactacat gaacctcaac cagaacccgc ggacgctgct gcccaagttc    660

tatgggctgt actgcgtgca gtcggggggc aagaacatcc gcgtcgtggt catgaacaac    720

atcctgcccc gcgtggtcaa gatgcacctc aagttcgacc tcaagggctc cacctacaag    780

cggcgcgcca gcaagaagga gaaggagaag agcttcccca cctacaagga cctggacttc    840

atgcaggaca tgcccgaggg gctcctgctg gacgccgaca ccttcagcgc cctggtcaag    900

acgctgcagc gggactgcct ggtcctggaa agtttcaaga tcatggacta cagcctgctg    960

ctgggcgtgc acaacatcga ccagcacgag cgcgagcggc aggcgcaggg cgcccagagc   1020

acctcagatg agaagcggcc tgtgggccag aaggcgctct actccacggc catggagtcc   1080

atccagggtg gcgccgcgcg cggggaggcc atcgaatcgg atgacacgat gggcgggatc   1140

cccgctgtga acggccgcgg ggagcggctg ctgctgcaca ttggcatcat cgacatcctg   1200

cagtcctaca ggttcatcaa gaaactggag cacacctgga aggccctcgt ccacgatggg   1260

gacacggtgt ccgtccaccg ccccagcttc tatgccgagc gctttttcaa gttcatgagc   1320

aacacggtct ttcggaagaa ctcctccctg aagtcctcgc cctccaagaa ggggcgcggc   1380

ggagccttgc tagctgtgaa accgctgggg cccaccgctg ccttctcggc cagccagatc   1440

cctagcgagc gggaggaggc ccagtacgac ctgcgggggg cccgcagcta ccccacgctg   1500

gaggacgaag gccggcccga cctcctgccc tgcacgccac cttctttcga agaagccact   1560

acagcctcca ttgccacgac tctgtcatcc acatccctct ccattcctga gcggtccccc   1620

tcggagacgt cggagcagcc gcggtacagg cggcgcacac agtcgtctgg acaggatggc   1680
```

```
aggccgcagg aggagccacc cgcggaagag gatctgcagc agattacagt gcaggtggag   1740

cctgcgtgca gcgtggagat tgtggtcccc aaagaggagg acgcaggggt ggaggcttcc   1800

ccggccggtg cctctgctgc tgttgaagta gaaactgcca gccaggcctc agacgaggag   1860

ggcgcacctg ccagccaggc ctcggacgag gaggacgcgc ccgccaccga catctacttt   1920

tggcgcctct ggggtcccca tgcacccacc tggccctgga gaagggaggg acgggccgcg   1980

tgcctgtgcc cctacccacc gcacgtcgtc accccttttc ctgggactgg tttgtgcgcg   2040

tcctggtctc cggatggtac ggggggcctg ggggccatgt cgtgctgtgt gtctgtgtcc   2100

tga                                                                  2103


<210> SEQ ID NO 2
<211> LENGTH: 2124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atggagctgg aggtaccgga cgaggcggag agcgctgagg cgggggccgt gccctcggag     60

gcggcgtggg cggcagagag cggggcggcg gcaggtttgg ctcagaagaa ggcggcccca    120

acagaggttc tgtccatgac ggcacagccg ggccctggcc atgggaagaa gttgggccat    180

cgaggtgtgg acgcatccgg cgaaaccacc tacaagaaga ccacctcctc caccctgaag    240

ggtgccatcc agctgggcat cggctacacc gtgggccacc tgagctccaa gcccgaacgc    300

gacgtgctca tgcaggactt ctacgtggtg gagagcatct tcttccccag cgaaggcagc    360

aacctcaccc ccgcccacca cttccaggac ttccgcttca agacctatgc acctgtcgcc    420

ttccgctact tccgggagct ctttgggatc cggccagatg attacttgta ctccctgtgc    480

aatgagccgc tgatcgagct gtccaacccg ggcgccagtg gctccctctt ctacgtcacc    540

agcgacgacg agttcatcat caagaccgtc atgcacaagg aggccgagtt cctgcagaag    600

ctgctccctg gctactacat gaacctcaac cagaacccgc ggacgctgct gcccaagttc    660

tatgggctgt actgcgtgca gtcggggggc aagaacatcc gcgtcgtggt catgaacaac    720

atcctgcccc gcgtggtcaa gatgcacctc aagttcgacc tcaagggctc cacctacaag    780

cggcgcgcca gcaagaagga gaaggagaag agcttcccca cctacaagga cctggacttc    840

atgcaggaca tgcccgaggg gctcctgctg gacgccgaca ccttcagcgc cctggtcaag    900

acgctgcagc gggactgcct ggtcctggaa agtttcaaga tcatggacta cagcctgctg    960

ctgggcgtgc acaacatcga ccagcacgag cgcgagcggc aggcgcaggg cgcccagagc   1020

acctcagatg agaagcggcc tgtgggccag aaggcgctct actccacggc catggagtcc   1080

atccagggtg gcgccgcgcg cggggaggcc atcgaatcgg atgacacgat gggcgggatc   1140

cccgctgtga acggccgcgg ggagcggctg ctgctgcaca ttggcatcat cgacatcctg   1200

cagtcctaca ggttcatcaa gaaactggag cacacctgga aggccctcgt ccacgatggg   1260

gacacggtgt ccgtccaccg ccccagcttc tatgccgagc gctttttcaa gttcatgagc   1320

aacacggtct ttcggaagaa ctcctccctg aagtcctcgc cctccaagaa ggggcgcggc   1380

ggagccttgc tagctgtgaa accgctgggg cccaccgctg ccttctcggc cagccagatc   1440

cctagcgagc gggaggaggc ccagtacgac ctgcgggggg cccgcagcta ccccacgctg   1500

gaggacgaag gccggcccga cctcctgccc tgcacgccac cttctttcga agaagccact   1560
```

acagcctcca ttgccacgac tctgtcatcc acatccctct ccattcctga gcggtccccc 1620
tcggagacgt cggagcagcc gcggtacagg cggcgcacac agtcgtctgg acaggatggc 1680
aggccgcagg aggagccacc cgcggaagag gatctgcagc agattacagt gcaggtggag 1740
cctgcgtgca gcgtggagat tgtggtcccc aaagaggagg acgcaggggt ggaggcttcc 1800
ccggccggtg cctctgctgc tgttgaagta gaaactgcca gccaggcctc agacgaggag 1860
ggcgcacctg ccagccaggc ctcggacgag gaggacgcgc ccgccaccga catctacttt 1920
ttcacggatg ggaggtactg gatttactct ccccgccatc gccgactgcg ggccgtgacg 1980
ctgagcgcct cggggactgt aagtgaccgc agccggccac cctggggaga aggggcagtg 2040
cccctcgggc agcagggagc cgcaggtccc cggccggaag ctcagtgtct gacgtcagtt 2100
gttttccaga agggctttgg gtaa 2124

<210> SEQ ID NO 3
<211> LENGTH: 700
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Met Glu Leu Glu Val Pro Asp Glu Ala Glu Ser Ala Glu Ala Gly Ala
1 5 10 15

Val Pro Ser Glu Ala Ala Trp Ala Ala Glu Ser Gly Ala Ala Ala Gly
20 25 30

Leu Ala Gln Lys Lys Ala Ala Pro Thr Glu Val Leu Ser Met Thr Ala
35 40 45

Gln Pro Gly Pro Gly His Gly Lys Lys Leu Gly His Arg Gly Val Asp
50 55 60

Ala Ser Gly Glu Thr Thr Tyr Lys Lys Thr Thr Ser Ser Thr Leu Lys
65 70 75 80

Gly Ala Ile Gln Leu Gly Ile Gly Tyr Thr Val Gly His Leu Ser Ser
85 90 95

Lys Pro Glu Arg Asp Val Leu Met Gln Asp Phe Tyr Val Val Glu Ser
100 105 110

Ile Phe Phe Pro Ser Glu Gly Ser Asn Leu Thr Pro Ala His His Phe
115 120 125

Gln Asp Phe Arg Phe Lys Thr Tyr Ala Pro Val Ala Phe Arg Tyr Phe
130 135 140

Arg Glu Leu Phe Gly Ile Arg Pro Asp Asp Tyr Leu Tyr Ser Leu Cys
145 150 155 160

Asn Glu Pro Leu Ile Glu Leu Ser Asn Pro Gly Ala Ser Gly Ser Leu
165 170 175

Phe Tyr Val Thr Ser Asp Asp Glu Phe Ile Ile Lys Thr Val Met His
180 185 190

Lys Glu Ala Glu Phe Leu Gln Lys Leu Leu Pro Gly Tyr Tyr Met Asn
195 200 205

Leu Asn Gln Asn Pro Arg Thr Leu Leu Pro Lys Phe Tyr Gly Leu Tyr
210 215 220

Cys Val Gln Ser Gly Gly Lys Asn Ile Arg Val Val Val Met Asn Asn
225 230 235 240

Ile Leu Pro Arg Val Val Lys Met His Leu Lys Phe Asp Leu Lys Gly
245 250 255

```
Ser Thr Tyr Lys Arg Arg Ala Ser Lys Lys Glu Lys Glu Lys Ser Phe
            260                 265                 270

Pro Thr Tyr Lys Asp Leu Asp Phe Met Gln Asp Met Pro Glu Gly Leu
        275                 280                 285

Leu Leu Asp Ala Asp Thr Phe Ser Ala Leu Val Lys Thr Leu Gln Arg
    290                 295                 300

Asp Cys Leu Val Leu Glu Ser Phe Lys Ile Met Asp Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
            340                 345                 350

Leu Tyr Ser Thr Ala Met Glu Ser Ile Gln Gly Gly Ala Ala Arg Gly
        355                 360                 365

Glu Ala Ile Glu Ser Asp Asp Thr Met Gly Gly Ile Pro Ala Val Asn
    370                 375                 380

Gly Arg Gly Glu Arg Leu Leu Leu His Ile Gly Ile Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
        435                 440                 445

Ser Leu Lys Ser Ser Pro Ser Lys Lys Gly Arg Gly Gly Ala Leu Leu
    450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
            500                 505                 510

Pro Pro Ser Phe Glu Glu Ala Thr Thr Ala Ser Ile Ala Thr Thr Leu
        515                 520                 525

Ser Ser Thr Ser Leu Ser Ile Pro Glu Arg Ser Pro Ser Glu Thr Ser
    530                 535                 540

Glu Gln Pro Arg Tyr Arg Arg Arg Thr Gln Ser Ser Gly Gln Asp Gly
545                 550                 555                 560

Arg Pro Gln Glu Glu Pro Pro Ala Glu Glu Asp Leu Gln Gln Ile Thr
                565                 570                 575

Val Gln Val Glu Pro Ala Cys Ser Val Glu Ile Val Val Pro Lys Glu
            580                 585                 590

Glu Asp Ala Gly Val Glu Ala Ser Pro Ala Gly Ala Ser Ala Ala Val
        595                 600                 605

Glu Val Glu Thr Ala Ser Gln Ala Ser Asp Glu Glu Gly Ala Pro Ala
    610                 615                 620

Ser Gln Ala Ser Asp Glu Glu Asp Ala Pro Ala Thr Asp Ile Tyr Phe
625                 630                 635                 640

Trp Arg Leu Trp Gly Pro His Ala Pro Thr Trp Pro Trp Arg Arg Glu
                645                 650                 655

Gly Arg Ala Ala Cys Leu Cys Pro Tyr Pro Pro His Val Val Thr Pro
            660                 665                 670
```

```
Phe Pro Gly Thr Gly Leu Cys Ala Ser Trp Ser Pro Asp Gly Thr Gly
        675                 680                 685

Gly Leu Gly Ala Met Ser Cys Cys Val Ser Val Ser
    690                 695                 700


<210> SEQ ID NO 4
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Glu Leu Glu Val Pro Asp Glu Ala Glu Ser Ala Glu Ala Gly Ala
1               5                   10                  15

Val Pro Ser Glu Ala Ala Trp Ala Ala Glu Ser Gly Ala Ala Ala Gly
            20                  25                  30

Leu Ala Gln Lys Lys Ala Ala Pro Thr Glu Val Leu Ser Met Thr Ala
        35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
            100                 105                 110

Ile Phe Phe Pro Ser Glu Gly Ser Asn Leu Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Val Met Asn Asn
225                 230                 235                 240

Ile Leu Pro Arg Val Val Lys Met His Leu Lys Phe Asp Leu Lys Gly
                245                 250                 255

Ser Thr Tyr Lys Arg Arg Ala Ser Lys Lys Glu Lys Glu Lys Ser Phe
            260                 265                 270

Pro Thr Tyr Lys Asp Leu Asp Phe Met Gln Asp Met Pro Glu Gly Leu
        275                 280                 285

Leu Leu Asp Ala Asp Thr Phe Ser Ala Leu Val Lys Thr Leu Gln Arg
    290                 295                 300

Asp Cys Leu Val Leu Glu Ser Phe Lys Ile Met Asp Tyr Ser Leu Leu
305                 310                 315                 320

Leu Gly Val His Asn Ile Asp Gln His Glu Arg Glu Arg Gln Ala Gln
                325                 330                 335
```

```
Gly Ala Gln Ser Thr Ser Asp Glu Lys Arg Pro Val Gly Gln Lys Ala
            340                 345                 350

Leu Tyr Ser Thr Ala Met Glu Ser Ile Gln Gly Gly Ala Ala Arg Gly
        355                 360                 365

Glu Ala Ile Glu Ser Asp Asp Thr Met Gly Gly Ile Pro Ala Val Asn
    370                 375                 380

Gly Arg Gly Glu Arg Leu Leu Leu His Ile Gly Ile Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
        435                 440                 445

Ser Leu Lys Ser Ser Pro Ser Lys Lys Gly Arg Gly Gly Ala Leu Leu
    450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
            500                 505                 510

Pro Pro Ser Phe Glu Glu Ala Thr Thr Ala Ser Ile Ala Thr Thr Leu
        515                 520                 525

Ser Ser Thr Ser Leu Ser Ile Pro Glu Arg Ser Pro Ser Glu Thr Ser
    530                 535                 540

Glu Gln Pro Arg Tyr Arg Arg Arg Thr Gln Ser Ser Gly Gln Asp Gly
545                 550                 555                 560

Arg Pro Gln Glu Glu Pro Pro Ala Glu Glu Asp Leu Gln Gln Ile Thr
                565                 570                 575

Val Gln Val Glu Pro Ala Cys Ser Val Glu Ile Val Val Pro Lys Glu
            580                 585                 590

Glu Asp Ala Gly Val Glu Ala Ser Pro Ala Gly Ala Ser Ala Ala Val
        595                 600                 605

Glu Val Glu Thr Ala Ser Gln Ala Ser Asp Glu Glu Gly Ala Pro Ala
    610                 615                 620

Ser Gln Ala Ser Asp Glu Glu Asp Ala Pro Ala Thr Asp Ile Tyr Phe
625                 630                 635                 640

Phe Thr Asp Gly Arg Tyr Trp Ile Tyr Ser Pro Arg His Arg Arg Leu
                645                 650                 655

Arg Ala Val Thr Leu Ser Ala Ser Gly Thr Val Ser Asp Arg Ser Arg
            660                 665                 670

Pro Pro Trp Gly Glu Gly Ala Val Pro Leu Gly Gln Gln Gly Ala Ala
        675                 680                 685

Gly Pro Arg Pro Glu Ala Gln Cys Leu Thr Ser Val Val Phe Gln Lys
    690                 695                 700

Gly Phe Gly
705


<210> SEQ ID NO 5
<211> LENGTH: 183
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 5
tggcgcctct ggggtcccca tgcacccacc tggccctgga gaagggaggg acgggccgcg 60
tgcctgtgcc cctacccacc gcacgtcgtc accccttttc ctgggactgg tttgtgcgcg 120
tcctggtctc cggatggtac gggggcctg ggggccatgt cgtgctgtgt gtctgtgtcc 180
tga 183

<210> SEQ ID NO 6
<211> LENGTH: 60
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Trp Arg Leu Trp Gly Pro His Ala Pro Thr Trp Pro Trp Arg Arg Glu
1 5 10 15

Gly Arg Ala Ala Cys Leu Cys Pro Tyr Pro Pro His Val Val Thr Pro
20 25 30

Phe Pro Gly Thr Gly Leu Cys Ala Ser Trp Ser Pro Asp Gly Thr Gly
35 40 45

Gly Leu Gly Ala Met Ser Cys Cys Val Ser Val Ser
50 55 60

<210> SEQ ID NO 7
<211> LENGTH: 204
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
ttcacggatg ggaggtactg gatttactct ccccgccatc gccgactgcg ggccgtgacg 60
ctgagcgcct cggggactgt aagtgaccgc agccggccac cctggggaga aggggcagtg 120
cccctcgggc agcagggagc cgcaggtccc cggccggaag ctcagtgtct gacgtcagtt 180
gttttccaga agggctttgg gtaa 204

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Phe Thr Asp Gly Arg Tyr Trp Ile Tyr Ser Pro Arg His Arg Arg Leu
1 5 10 15

Arg Ala Val Thr Leu Ser Ala Ser Gly Thr Val Ser Asp Arg Ser Arg
20 25 30

Pro Pro Trp Gly Glu Gly Ala Val Pro Leu Gly Gln Gln Gly Ala Ala
35 40 45

Gly Pro Arg Pro Glu Ala Gln Cys Leu Thr Ser Val Val Phe Gln Lys
50 55 60

Gly Phe Gly

65

<210> SEQ ID NO 9
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Ala Ala Val Pro Glu Leu Leu Gln Gln Gln Glu Glu Asp Arg Ser
1               5                   10                  15

Lys Leu Arg Ser Val Ser Val Asp Leu Asn Val Asp Pro Ser Leu Gln
            20                  25                  30

Ile Asp Ile Pro Asp Ala Leu Ser Glu Arg Asp Lys Val Lys Phe Thr
        35                  40                  45

Val His Thr Lys Thr Thr Leu Pro Thr Phe Gln Ser Pro Glu Phe Ser
    50                  55                  60

Val Thr Arg Gln His Glu Asp Phe Val Trp Leu His Asp Thr Leu Ile
65                  70                  75                  80

Glu Thr Thr Asp Tyr Ala Gly Leu Ile Ile Pro Pro Ala Pro Thr Lys
                85                  90                  95

Pro Asp Phe Asp Gly Pro Arg Glu Lys Met Gln Lys Leu Gly Glu Gly
            100                 105                 110

Glu Gly Ser Met Thr Lys Glu Glu Phe Ala Lys Met Lys Gln Glu Leu
        115                 120                 125

Glu Ala Glu Tyr Leu Ala Val Phe Lys Lys Thr Val Ser Ser His Glu
    130                 135                 140

Val Phe Leu Gln Arg Leu Ser Ser His Pro Val Leu Ser Lys Asp Arg
145                 150                 155                 160

Asn Phe His Val Phe Leu Glu Tyr Asp Gln Asp Leu Ser Val Arg Arg
                165                 170                 175

Lys Asn Thr Lys Glu Met Phe Gly Gly Phe Phe Lys Ser Val Val Lys
            180                 185                 190

Ser Ala Asp Glu Val Leu Phe Thr Gly Val Lys Glu Val Asp Asp Phe
        195                 200                 205

Phe Glu Gln Glu Lys Asn Phe Leu Ile Asn Tyr Tyr Asn Arg Ile Lys
    210                 215                 220

Asp Ser Cys Val Lys Ala Asp Lys Met Thr Arg Ser His Lys Asn Val
225                 230                 235                 240

Ala Asp Asp Tyr Ile His Thr Ala Ala Cys Leu His Ser Leu Ala Leu
                245                 250                 255

Glu Glu Pro Thr Val Ile Lys Lys Tyr Leu Leu Lys Val Ala Glu Leu
            260                 265                 270

Phe Glu Lys Leu Arg Lys Val Glu Gly Arg Val Ser Ser Asp Glu Asp
        275                 280                 285

Leu Lys Leu Thr Glu Leu Leu Arg Tyr Tyr Met Leu Asn Ile Glu Ala
    290                 295                 300

Ala Lys Asp Leu Leu Tyr Arg Arg Thr Lys Ala Leu Ile Asp Tyr Glu
305                 310                 315                 320

Asn Ser Asn Lys Ala Leu Asp Lys Ala Arg Leu Lys Ser Lys Asp Val
                325                 330                 335

Lys Leu Ala Glu Ala His Gln Gln Glu Cys Cys Gln Lys Phe Glu Gln
            340                 345                 350
```

```
Leu Ser Glu Ser Ala Lys Glu Glu Leu Ile Asn Phe Lys Arg Lys Arg
        355                 360                 365

Val Ala Ala Phe Arg Lys Asn Leu Ile Glu Met Ser Glu Leu Glu Ile
    370                 375                 380

Lys His Ala Arg Asn Asn Val Ser Leu Leu Gln Ser Cys Ile Asp Leu
385                 390                 395                 400

Phe Lys Asn Asn


<210> SEQ ID NO 10
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Val Asn Pro Gly Ser Ser Ser Gln Pro Pro Pro Val Thr Ala Gly
1               5                   10                  15

Ser Leu Ser Trp Lys Arg Cys Ala Gly Cys Gly Gly Lys Ile Ala Asp
            20                  25                  30

Arg Phe Leu Leu Tyr Ala Met Asp Ser Tyr Trp His Ser Arg Cys Leu
        35                  40                  45

Lys Cys Ser Cys Cys Gln Ala Gln Leu Gly Asp Ile Gly Thr Ser Cys
    50                  55                  60

Tyr Thr Lys Ser Gly Met Ile Leu Cys Arg Asn Asp Tyr Ile Arg Leu
65                  70                  75                  80

Phe Gly Asn Ser Gly Ala Cys Ser Ala Cys Gly Gln Ser Ile Pro Ala
                85                  90                  95

Ser Glu Leu Val Met Arg Ala Gln Gly Asn Val Tyr His Leu Lys Cys
            100                 105                 110

Phe Thr Cys Ser Thr Cys Arg Asn Arg Leu Val Pro Gly Asp Arg Phe
        115                 120                 125

His Tyr Ile Asn Gly Ser Leu Phe Cys Glu His Asp Arg Pro Thr Ala
    130                 135                 140

Leu Ile Asn Gly His Leu Asn Ser Leu Gln Ser Asn Pro Leu Leu Pro
145                 150                 155                 160

Asp Gln Lys Val Cys
                165


<210> SEQ ID NO 11
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Leu Glu Val Pro Asp Glu Ala Glu Ser Ala Glu Ala Gly Ala
1               5                   10                  15

Val Pro Ser Glu Ala Ala Trp Ala Ala Glu Ser Gly Ala Ala Ala Gly
            20                  25                  30

Leu Ala Gln Lys Lys Ala Ala Pro Thr Glu Val Leu Ser Met Thr Ala
        35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
```

-continued

```
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
            100                 105                 110

Ile Phe Phe Pro Ser Glu Gly Ser Asn Leu Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Val Met Asn Asn
225                 230                 235                 240

Ile Leu Pro Arg Val Val Lys Met His Leu Lys Phe Asp Leu Lys Gly
                245                 250                 255

Ser Thr Tyr Lys Arg Arg Ala Ser Lys Lys Glu Lys Glu Lys Ser Phe
            260                 265                 270

Pro Thr Tyr Lys Asp Leu Asp Phe Met Gln Asp Met Pro Glu Gly Leu
        275                 280                 285

Leu Leu Asp Ala Asp Thr Phe Ser Ala Leu Val Lys Thr Leu Gln Arg
    290                 295                 300

Asp Cys Leu Val Leu Glu Ser Phe Lys Ile Met Ala Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
            340                 345                 350

Leu Tyr Ser Thr Ala Met Glu Ser Ile Gln Gly Gly Ala Ala Arg Gly
        355                 360                 365

Glu Ala Ile Glu Ser Asp Asp Thr Met Gly Gly Ile Pro Ala Val Asn
    370                 375                 380

Gly Arg Gly Glu Arg Leu Leu Leu His Ile Gly Ile Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
        435                 440                 445

Ser Leu Lys Ser Ser Pro Ser Lys Lys Gly Arg Gly Gly Ala Leu Leu
    450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495
```

Tyr Pro Thr Leu Glu Asp Glu Gly Arg Pro Asp Leu Leu Pro Cys Thr
500 505 510

Pro Pro Ser Phe Glu Glu Ala Thr Thr Ala Ser Ile Ala Thr Thr Leu
515 520 525

Ser Ser Thr Ser Leu Ser Ile Pro Glu Arg Ser Pro Ser Glu Thr Ser
530 535 540

Glu Gln Pro Arg Tyr Arg Arg Arg Thr Gln Ser Ser Gly Gln Asp Gly
545 550 555 560

Arg Pro Gln Glu Glu Pro Pro Ala Glu Glu Asp Leu Gln Gln Ile Thr
565 570 575

Val Gln Val Glu Pro Ala Cys Ser Val Glu Ile Val Val Pro Lys Glu
580 585 590

Glu Asp Ala Gly Val Glu Ala Ser Pro Ala Gly Ala Ser Ala Ala Val
595 600 605

Glu Val Glu Thr Ala Ser Gln Ala Ser Asp Glu Glu Gly Ala Pro Ala
610 615 620

Ser Gln Ala Ser Asp Glu Glu Asp Ala Pro Ala Thr Asp Ile Tyr Phe
625 630 635 640

Trp Arg Leu Trp Gly Pro His Ala Pro Thr Trp Pro Trp Arg Arg Glu
645 650 655

Gly Arg Ala Ala Cys Leu Cys Pro Tyr Pro Pro His Val Val Thr Pro
660 665 670

Phe Pro Gly Thr Gly Leu Cys Ala Ser Trp Ser Pro Asp Gly Thr Gly
675 680 685

Gly Leu Gly Ala Met Ser Cys Cys Val Ser Val Ser
690 695 700

<210> SEQ ID NO 12
<211> LENGTH: 707
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Glu Leu Glu Val Pro Asp Glu Ala Glu Ser Ala Glu Ala Gly Ala
1 5 10 15

Val Pro Ser Glu Ala Ala Trp Ala Ala Glu Ser Gly Ala Ala Ala Gly
20 25 30

Leu Ala Gln Lys Lys Ala Ala Pro Thr Glu Val Leu Ser Met Thr Ala
35 40 45

Gln Pro Gly Pro Gly His Gly Lys Lys Leu Gly His Arg Gly Val Asp
50 55 60

Ala Ser Gly Glu Thr Thr Tyr Lys Lys Thr Thr Ser Ser Thr Leu Lys
65 70 75 80

Gly Ala Ile Gln Leu Gly Ile Gly Tyr Thr Val Gly His Leu Ser Ser
85 90 95

Lys Pro Glu Arg Asp Val Leu Met Gln Asp Phe Tyr Val Val Glu Ser
100 105 110

Ile Phe Phe Pro Ser Glu Gly Ser Asn Leu Thr Pro Ala His His Phe
115 120 125

Gln Asp Phe Arg Phe Lys Thr Tyr Ala Pro Val Ala Phe Arg Tyr Phe
130 135 140

Arg Glu Leu Phe Gly Ile Arg Pro Asp Asp Tyr Leu Tyr Ser Leu Cys

-continued

```
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Val Met Asn Asn
225                 230                 235                 240

Ile Leu Pro Arg Val Val Lys Met His Leu Lys Phe Asp Leu Lys Gly
                245                 250                 255

Ser Thr Tyr Lys Arg Arg Ala Ser Lys Lys Glu Lys Glu Lys Ser Phe
            260                 265                 270

Pro Thr Tyr Lys Asp Leu Asp Phe Met Gln Asp Met Pro Glu Gly Leu
        275                 280                 285

Leu Leu Asp Ala Asp Thr Phe Ser Ala Leu Val Lys Thr Leu Gln Arg
    290                 295                 300

Asp Cys Leu Val Leu Glu Ser Phe Lys Ile Met Ala Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
            340                 345                 350

Leu Tyr Ser Thr Ala Met Glu Ser Ile Gln Gly Gly Ala Ala Arg Gly
        355                 360                 365

Glu Ala Ile Glu Ser Asp Asp Thr Met Gly Gly Ile Pro Ala Val Asn
    370                 375                 380

Gly Arg Gly Glu Arg Leu Leu Leu His Ile Gly Ile Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
        435                 440                 445

Ser Leu Lys Ser Ser Pro Ser Lys Lys Gly Arg Gly Gly Ala Leu Leu
    450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
            500                 505                 510

Pro Pro Ser Phe Glu Glu Ala Thr Thr Ala Ser Ile Ala Thr Thr Leu
        515                 520                 525

Ser Ser Thr Ser Leu Ser Ile Pro Glu Arg Ser Pro Ser Glu Thr Ser
    530                 535                 540

Glu Gln Pro Arg Tyr Arg Arg Arg Thr Gln Ser Ser Gly Gln Asp Gly
545                 550                 555                 560

Arg Pro Gln Glu Glu Pro Pro Ala Glu Glu Asp Leu Gln Gln Ile Thr
                565                 570                 575
```

```
Val Gln Val Glu Pro Ala Cys Ser Val Glu Ile Val Val Pro Lys Glu
            580                 585                 590

Glu Asp Ala Gly Val Glu Ala Ser Pro Ala Gly Ala Ser Ala Ala Val
        595                 600                 605

Glu Val Glu Thr Ala Ser Gln Ala Ser Asp Glu Glu Gly Ala Pro Ala
    610                 615                 620

Ser Gln Ala Ser Asp Glu Glu Asp Ala Pro Ala Thr Asp Ile Tyr Phe
625                 630                 635                 640

Phe Thr Asp Gly Arg Tyr Trp Ile Tyr Ser Pro Arg His Arg Arg Leu
                645                 650                 655

Arg Ala Val Thr Leu Ser Ala Ser Gly Thr Val Ser Asp Arg Ser Arg
            660                 665                 670

Pro Pro Trp Gly Glu Gly Ala Val Pro Leu Gly Gln Gln Gly Ala Ala
        675                 680                 685

Gly Pro Arg Pro Glu Ala Gln Cys Leu Thr Ser Val Val Phe Gln Lys
    690                 695                 700

Gly Phe Gly
705


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

atggagctgg aggtaccgga                                                20


<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

ttacccaaag cccttctgga aa                                             22


<210> SEQ ID NO 15
<211> LENGTH: 69
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Phe Phe Thr Asp Gly Arg Tyr Trp Ile Tyr Ser Pro Arg His Arg
1               5                   10                  15

Arg Leu Arg Ala Val Thr Leu Ser Ala Ser Gly Thr Val Ser Asp Arg
            20                  25                  30

Ser Arg Pro Pro Trp Gly Glu Gly Ala Val Pro Leu Gly Gln Gln Gly
        35                  40                  45

Ala Ala Gly Pro Arg Pro Glu Ala Gln Cys Leu Thr Ser Val Val Phe
    50                  55                  60

Gln Lys Gly Phe Gly
65
```

-continued

```
<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Phe Pro Thr Asp Glu Arg Ser Trp Val Tyr Ser Pro Leu His Tyr
1               5                   10                  15

Ser Ala Gln Ala Pro Pro Ala Ser Asp Gly Glu Ser Asp Thr
            20                  25                  30


<210> SEQ ID NO 17
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Phe Trp Arg Leu Trp Gly Pro His Ala Pro Thr Trp Pro Trp Arg
1               5                   10                  15

Arg Glu Gly Arg Ala Ala Cys Leu Cys Pro Tyr Pro Pro His Val Val
            20                  25                  30

Thr Pro Phe Pro Gly Thr Gly Leu Cys Ala Ser Trp Ser Pro Asp Gly
        35                  40                  45

Thr Gly Gly Leu Gly Ala Met Ser Cys Cys Val Ser Val Ser
    50                  55                  60
```

PHOSPHATIDYLINOSITOL PHOSPHATE KINASE TYPE 1 GAMMA SPLICE VARIANTS AS BIOMARKERS AND DRUG TARGETS FOR EPITHELIAL CANCERS

CROSS-REFERENCE TO RELATED PATENT APPLICATIONS

This application is a divisional of U.S. application Ser. No. 12/243,664, filed Oct. 1, 2008, which claims the benefit of U.S. Provisional Application 60/976,928, filed on Oct. 2, 2007, both of which are incorporated herein by reference in their entireties.

GOVERNMENT SUPPORT

This invention was made with government support under GM057549 and CA104708, awarded by the National Institutes of Health. The United States government has certain rights in the invention.

FIELD OF THE INVENTION

The present invention relates generally to the field of phosphatidylinositol based signaling pathways, and more specifically to the use of novel members of these pathways for disease prognosis and treatment. In some aspects, the present invention relates to the use of novel splice variants of type I phosphatidylinositol phosphate kinase γ to determine breast cancer and breast cancer prognosis.

BACKGROUND OF THE INVENTION

The following discussion of the background is merely provided to aid the reader in understanding the invention and is not admitted to describe or constitute prior art to the invention.

In mammalian cells, there are two types of phosphatidylinositol phosphate kinases: Type I and Type II. Both types serve to produce various phosphoinositides, phospholipid second messengers which are important in a variety of cellular functions ranging from cell motility to focal adhesion assembly to protein trafficking. Type I phosphatidylinositol phosphate kinase ("PIPKI") exists in at least three isoforms—α, β, and γ. These isoforms are the major producers of a second messenger named phosphatidylinositol-4,5-bisphosphate ("PI4,5$P_2$"). PI4,5$P_2$ is a membrane phospholipid which plays a role in many cellular signaling pathways. Even though PI4,5$P_2$ is maintained at relatively constant levels in cells, it is hypothesized that small local changes in the spatial and temporal synthesis of PI4,5$P_2$ defines its role as a second messenger.

The different PIPKI isoforms are differentially expressed spatially and temporally, thereby providing a mechanism for control of PI4,5$P_2$ generation. The C-termini of the PIPKIs are sequence divergent, indicating that this region may be important for functional divergence. Further, each type I PIP kinase isoform mRNA transcript may be alternatively spliced, thereby resulting in multiple splice variants, each differentially localized for specific cellular functions. Thus, the distinct localization and targeting of these different kinase isoforms allows for PI4,5$P_2$ production at specific sites throughout the cell, resulting in spatial and temporal regulation of multiple cellular processes. Such localization may be facilitated by the interaction of the PIP kinases with protein partners capable of targeting the kinase to specific sub-cellular compartments. Interestingly, many of these protein partners are themselves PI4,5$P_2$ effectors.

Accordingly, the identification and characterization of novel PIP kinases which affect the expression levels or localization of second messengers such as PI4,5$P_2$ would be an important step in further elucidating phosphatidylinositol based signaling pathways. Here, two novel human PIPKIγ splice variants, termed PIPKIγ 700 and PIPKIγ 707, are described.

SUMMARY OF THE INVENTION

The compositions, methods and kits described herein relate to novel PIPKIγ splice variants, termed PIPKIγ 700 and PIPKIγ 707, and the use of these novel variants to detect, diagnose, monitor and determine a prognosis for some types of oncongenic conditions in a subject. In particular, the novel kinases may be used to detect, monitor and determine a prognosis for epithelial cancers, such as breast, ovarian, uterine, prostate and skin cancers in a mammal. In some embodiments, the mammal is a human and a first example of a cancer is breast cancer.

Compositions described herein include isolated polynucleotides encoding novel PIPKIγ 700 and PIPKIγ 707 polypeptides and their homologues, wherein the polypeptides have lipid kinase activity. Other embodiments include isolated polynucleotides encoding fragments of the novel PIPKIγ 700 and/or PIPKIγ 707 polypeptides, their homologues and variants. In still other embodiments, complements to such polynucleotides are included.

In some embodiments, the polynucleotide sequence encoding a polypeptide sequence includes at least about 50%, at least about 60%, at least about 70%, at least about 80%, at least about 90% or at least about 95% sequence identity to SEQ ID NO: 3, 4, 6 or 8. In other embodiments, the polynucleotide sequence includes SEQ ID NO: 1, 2, 5 or 7; in still other embodiments, the polynucleotide sequence is degenerate to SEQ ID NO 1, 2, 5 or 7 due to the genetic code (i.e., the polynucleotide encodes the same amino acid sequence as SEQ ID NO: 1, 2, 5 or 7, but comprises a different nucleic acid sequence than SEQ ID NO: 1, 2, 5 or 7). In yet further embodiments, the polynucleotides sequence has at least about 50%, at least about 60%, at least about 70%, at least about 80%, at least about 90% or at least about 95% sequence identity to SEQ ID NO: 1, 2, 5 or 7.

Compositions described herein also include polynucleotides encoding fragments, domains or functional fragments of the novel kinases PIPKIγ 700 and PIPKIγ 707. In other embodiments, polynucleotides include complements of such fragments. For example, polynucleotides encoding the polypeptides of the C-terminal of PIPKIγ 700 (e.g., SEQ ID NO:5) and PIPKIγ 707 (e.g., SEQ ID NO:7) are included. In still other embodiments, polynucleotides encoding variants of these fragments, and polynucleotides encoding protein fusions including these fragments are described.

In some embodiments, the polynucleotide is a DNA molecule; in other embodiments, the polynucleotide is an RNA molecule. In some embodiments, the polynucleotide functions as a probe, a primer or as an siRNA molecule. In some embodiments, the polynucleotide includes one or more detectable labels, such as fluorescent or radioactive labels.

In further embodiments, a polynucleotide encoding a PIPKIγ 700, PIPKIγ 707 or fragment thereof is contained in a vector. In some embodiments, the vector is an expression vector. In some embodiments, the expression vectors include control sequences to which the polynucleotide is operably linked; accordingly, in some embodiments, the control sequence directs the production of a polypeptide. In still other embodiments, the vector is introduced into an isolated host cell. In some embodiments, the host cell is prokaryotic or eukaryotic. In other embodiments, the host cell is a bacterial cell, a yeast cell, a mammalian cell or a plant cell. In particular embodiments, host cells include bacterial cells, such as *Escherichia coli* cells.

In some embodiments, methods relate to producing a polypeptide encoding PIPKIγ 700, PIPKIγ 707, a fragment or variant thereof. In some embodiments, cells containing an expression vector carrying a polynucleotide encoding the PIPKIγ 700, PIPKIγ 707, a fragment or variant thereof are cultured under conditions suitable for expression of the polypeptide. In such embodiments, the polynucleotide encoding the polypeptide is operably linked to a promoter sequence. In some embodiments, the polypeptide so produced is isolated. In particular embodiments, the expressed polypeptide includes SEQ ID NO: 3, 4, 6 or 8, a fragment or a variant thereof; in other embodiments, expressed polypeptide is encoded by a polynucleotide which includes SEQ ID NO: 1, 2, 5 or 7, a fragment or a variant thereof.

Other aspects relate to polypeptide sequences encoding PIPKIγ 700, PIPKIγ 707 or functional fragments thereof. For example, in some embodiments, the polypeptide has lipid kinase activity. In some embodiments, the peptide has an amino acid sequence having at least about 50%, at least about 60%, at least about 70%, at least about 80%, at least about 90% or at least about 95% sequence identity with SEQ ID NO: 3, 4, 6 or 8. Additionally or alternatively, the polypeptide includes SEQ ID NO: 3, 4, 6 or 8.

Some aspects relate to antibodies capable of specifically binding to PIPKIγ 700, PIPKIγ 707 or fragments thereof; in some embodiments the antibody is a polyclonal antibody. In other embodiments, the antibody is a monoclonal antibody. In some embodiments, the antibody does not cross-react with any other PIPKIγ splice variants (e.g., a PIPKIγ 700 antibody does not does not cross react with PIPKIγ 640, 668, and PIPKIγ 707 polypeptides). In some embodiments the antibody specifically binds to a polypeptide including an amino acid sequence having at least about 50%, at least about 60%, at least about 70%, at least about 80%, at least about 90% or at least about 95% sequence identity to SEQ ID NO: 3 or 4 or a fragment thereof; in other embodiments, the antibody specifically binds to a polypeptide including an amino acid sequence having at least about 50%, at least about 60%, at least about 70%, at least about 80%, at least about 90% or at least about 95% sequence identity to SEQ ID NO: 6 or 8 or a fragment thereof. In further embodiments, the antibody specifically binds to an amino acid sequence SEQ ID NO: 3, 4, 6 or 8. In still further embodiments the polypeptide has lipid kinase activity.

In some aspects, the compositions, methods and kits relate to the prognostic evaluation of a subject suspected of having, or at risk of developing cancer. In some embodiments the cancer includes epithelial cancer, such as breast, ovarian, uterine and skin cancer, and the prognosis relates to patient survival.

In some embodiments, the prognostic methods include detecting any one of the polynucleotides of SEQ ID NO: 1, 2, 5 or 7, or naturally occurring variants thereof in a tissue sample of a subject. In other embodiments, the methods include a nucleic acid hybridization step to detect the polynucleotides. In some embodiments, the methods detect an RNA molecule. In other methods, a DNA molecule is detected.

In some embodiments, the polynucleotide (e.g., SEQ ID NO: 1, 2, 5 or 7) is detected in a tissue sample that is likely to be affected by the cancer, such as a breast tissue sample, taken from the subject. In other embodiments, the presence and/or amount of the detected sequence in the subject tissue may compared to the presence and/or amount of the same sequence (e.g., SEQ ID NO: 1, 2, 5 or 7) in control sample. In some embodiments, a control sample includes normal, non-cancerous tissue of the same type as the subject tissue sample. Control samples may be taken from the subject, or may be taken from a control subject. In some embodiments, a lower amount of detected sequence in the subject tissue sample as compared to the control tissue sample is indicative of a better prognosis (e.g., greater survival time) than a subject having equal or higher amounts of the detected sequence in the subject tissue sample as compared to the amount detected in a control tissue sample.

In some embodiments, prognostic methods include the detection of the nucleic acid of one or more cancer markers, such as HER1 and/or HER2 in conjunction with the detection of a polynucleotide of SEQ ID NO: 1, 2, 5 or 7 or fragments or variants thereof. In some embodiments, the methods include, for example, determining the amount of a cancer marker nucleic acid (e.g., HER1 and/or HER2 nucleic acid) in the subject tissue, and comparing this amount with the amount of the cancer marker in a control tissue sample. In some embodiments, a control sample includes normal, non-cancerous tissue of the same type as the subject tissue sample. In particular embodiments, a high level of HER1 and/or HER2 compared to control levels, in conjunction with normal to high level of PIPKIγ 700 and/or PIPKIγ 707 nucleic acid compared to control levels indicates a poor prognosis (e.g., shorter survival time). In still other embodiments, a high level of HER1 and/or HER2 compared to control HER levels in conjunction with a low level of PIPKIγ 700 and/or PIPKIγ 707 nucleic acid compared to control levels, indicates a better prognosis (e.g., longer survival time).

In other embodiments, the prognostic methods include detecting any one of the polypeptides of SEQ ID NO: 3, 4, 6 or 8, fragments or naturally occurring variants thereof. Some method include an antibody hybridization step to detect the polypeptide. In some embodiments, the antibody is a polyclonal antibody, a monoclonal antibody or a combination of both a polyclonal and a monoclonal antibody.

In some embodiments, the polypeptide is detected in a patient tissue sample, such as breast tissue, that is likely to be affected by a cancer, such breast cancer. In some embodiments, the presence and/or amount of the detected polypeptide in the subject tissue may compared to the presence and/or amount present in control sample. In some embodiments, a control sample includes normal, non-cancerous tissue of the same tissue type as the patient sample tissue. In some embodiments, a lower amount of detected polypeptide of SEQ ID NO: 3, 4, 6 or 8 in the subject sample compared to the control sample is indicative of a better prognosis (e.g., greater longevity).

Other methods include the detection of the polypeptide of one or more cancer markers, such as HER1 and/or HER2 in conjunction with the detection of a polypeptide of SEQ ID NO: 3, 4, 6 or 8 or variants thereof. In some embodiments, the methods include determining the amount of the cancer marker polypeptide (e.g., HER1 and/or HER2 polypeptide) in the subject sample tissue, and comparing this amount with the amount of the cancer marker (e.g., HER 1 and/or HER2) polypeptide present in control samples. In some embodiments, a control sample includes normal, non-cancerous tissue of the same type as the sample tissue. In other embodiments, a high level of the cancer marker (e.g., HER1 and/or HER2) compared to control levels in conjunction with a normal to high level of PIPKIγ 700, PIPKIγ 707 protein, indicates a poor prognosis. In still other embodiments, a high level of the cancer marker (e.g., HER1 and/or HER2) compared to control levels in conjunction with a low level of PIPKIγ 700, PIPKIγ 707 protein, indicates a better prognosis.

Also disclosed herein are methods to screen for agents which bind to PIPKIγ 700, PIPKIγ 707, a fragment, or variant thereof. In some methods, a polypeptide including PIPKIγ 700, PIPKIγ 707, a fragment or variants thereof is contacted, under suitable conditions, with one or more agents. Binding of the agent to the PIPKIγ 700, PIPKIγ 707, a fragment or a variant thereof is then detected. Such methods are performed in vitro or in vivo.

Further aspects include methods for identifying agents which modulate the activity of PIPKIγ 700, PIPKIγ 707, fragments or variants thereof. Such methods are performed in vivo or in vitro. In some embodiments, the methods include contacting PIPKIγ 707 with an agent in the presence of SNX5 and determining whether the activity or localization of SNX5 is modulated. In some embodiments, the agent does not directly modulate or interact with SNX5. In other embodiments the agent directly interacts with or modulates SNX5. In still other embodiments, a change in SNX5 activity or localization is indicative of the agent modulating PIPKIγ 707 activity.

In further embodiments, the methods include contacting PIPKIγ 700 with an agent in the presence of LMO4 and determining whether the agent modulates the activity of LMO4. In some embodiments, the agent does not directly modulate or interact with LMO4. In other embodiments, the agent directly interacts with or modulates LMO4. In still other embodiments, a change in LMO4 activity or localization is indicative of the agent modulating PIPKIγ 700 activity.

In other methods, PIPKIγ 700 or PIPKIγ 707 is contacted with an agent and the PIPKIγ 700 or PIPKIγ 707 kinase activity is determined and compared to control PIPKIγ 700 or PIPKIγ 707 kinase activity (e.g., PIPKIγ activity in the absence of the agent). If the kinase activity of the splice variant in contact with the agent increases, the agent is termed an enhancer. If the kinase activity of the splice variant in contact with the agent decreases, the agent is termed an inhibitor.

Other aspects described herein include kits. In some embodiments, the kit includes one or more nucleic acids useful for the detection of one or more of the following: 1) a polynucleotide encoding a polypeptide of SEQ ID NO: 3, 4, 6 or 8; 2) a polynucleotide sequence encoding a polypeptide including at least about 50%, at least about 60%, at least about 70%, at least about 80%, at least about 90% or at least about 95% sequence identity to SEQ ID NO: 3, 4, 6 or 8; 3) the polynucleotide sequence of SEQ ID NO: 1, 2, 5 or 7; 4) a polynucleotide sequence including at least about 50%, at least about 60%, at least about 70%, at least about 80%, at least about 90% or at least about 95% sequence identity to SEQ ID NO: 1, 2, 5 or 7. In other embodiments, kits include one or more of the following: 1) a polynucleotide encoding a polypeptide of SEQ ID NO: 3, 4, 6 or 8; 2) a polynucleotide sequence encoding a polypeptide including at least about 50%, at least about 60%, at least about 70%, at least about 80%, at least about 90% or at least about 95% sequence identity to SEQ ID NO: 3, 4, 6 or 8; 3) the polynucleotide sequence of SEQ ID NO: 1, 2, 5 or 7; 4) a polynucleotide sequence including at least about 50%, at least about 60%, at least about 70%, at least about 80%, at least about 90% or at least about 95% sequence identity to SEQ ID NO: 1, 2, 5 or 7.

In other embodiments, the kit includes an antibody capable of specifically binding to PIPKIγ 700, PIPKIγ 707, fragments, or variants thereof. In some embodiments, the antibody includes a monoclonal or a polyclonal antibody that specifically binds to an amino acid sequence having at least about 50%, at least about 60%, at least about 70%, at least about 80%, at least about 90% or at least about 95% sequence identity to SEQ ID NO: 3 or 4 or a fragment thereof. In other embodiments, the antibody includes a monoclonal or a polyclonal antibody that specifically binds to an amino acid sequence having at least about 50%, at least about 60%, at least about 70%, at least about 80%, at least about 90% or at least about 95% sequence identity to SEQ ID NO: 6 or 8 or a fragment thereof. In further embodiments, the kit includes a monoclonal or a polyclonal antibody that specifically binds to an amino acid sequence of SEQ ID NO: 3, 4, 6 or 8.

In still other embodiments, kits include polypeptides encoding a PIPKIγ 700 and/or PIPKIγ 707, fragments and variants thereof. In some embodiments, kits include one or more of the following: a polypeptide having at least about 50%, at least about 60%, at least about 70%, at least about 80%, at least about 90% or at least about 95% sequence identity to SEQ ID NO: 3 or 4 or a fragment thereof. In other embodiments, the polypeptide has an amino acid sequence having at least about 50%, 60%, 70%, 80%, 90% or at least about 95% sequence identity to SEQ ID NO: 6 or 8 or a fragment thereof. In further embodiments, polypeptide includes an amino acid sequence of SEQ ID NO: 3, 4, 6 or 8.

In some embodiments, kits also include test reaction reagents, control reagents and instruction for performing, troubleshooting and interpreting test reactions and results.

BRIEF DESCRIPTION OF THE DRAWINGS

FIG. 13 shows a table correlating known breast cancer biomarker expression with PIPKIγ expression in breast cancer samples.

FIG. 21 shows the PIPKIγ 700 nucleic acid sequence.
FIG. 22 shows the PIPKIγ 707 nucleic acid sequence.
FIG. 23 shows the PIPKIγ 700 amino acid sequence.
FIG. 24 shows the PIPKIγ 707 amino acid sequence.
FIG. 25 shows the PIPKIγ 700 C-terminal nucleic acid sequence.
FIG. 26 shows the PIPKIγ 700 C-terminal amino acid sequence.
FIG. 27 shows the PIPKIγ 707 C-terminal nucleic acid sequence.
FIG. 28 shows the PIPKIγ 707 C-terminal amino acid sequence.
FIG. 29 shows the SNX5 amino acid sequence.
FIG. 30 shows the LMO4 amino acid sequence.
FIG. 31 shows the kinase inactive PIPKIγ 700 D316A mutant amino acid sequence.
FIG. 32 shows the kinase inactive PIPKIγ 707 D316A mutant amino acid sequence.

DETAILED DESCRIPTION

Figure 1:
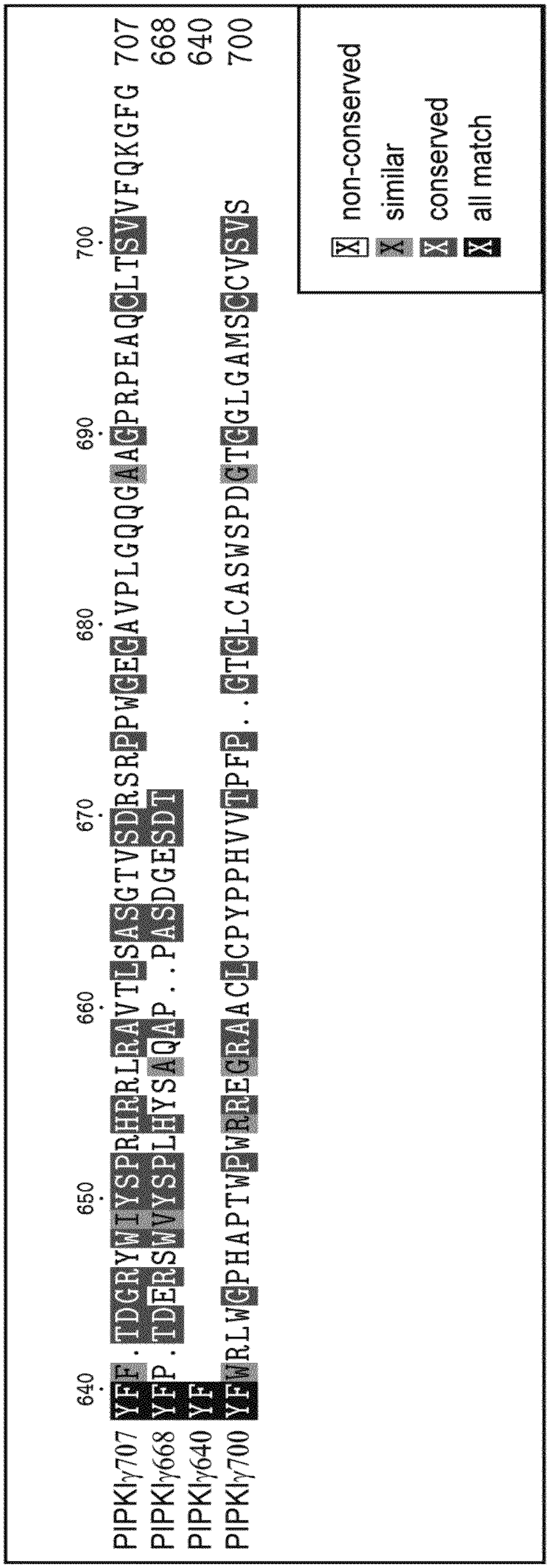
FIG. 1 shows the amino acid sequences of C-terminal region of four PIPKI-γhuman splice variants (SEQ ID NOS 15-17, respectively in order of appearance).

Disclosed herein are nucleic acids, proteins, expression vectors, antibodies and kits related to novel PIPKIγ splice variants. Also disclosed are methods describing the use of these novel variants to detect, diagnose, monitor and determine a prognosis for some types of oncogenic conditions such as epithelial cancers, for example, breast, ovarian, uterine, prostate and skin cancers. In some embodiments, a breast cancer prognosis is determined. Accordingly, the following discussion will describe some of the characteristics of these novel splice variants, their interactions with other proteins, and their use in cancer detection, treatment, monitoring and prognosis.

The present invention is described herein using several definitions, as set forth below and throughout the specification.

As used herein "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, unless otherwise stated, the singular forms "a," "an," and "the" includes plural reference. Thus, for example, a reference to "an oligonucleotide" includes a plurality of oligonucleotide molecules, and a reference to "a nucleic acid" is a reference to one or more nucleic acids.

As used herein, the term "subject" is refers to an animal, preferably a mammal, more preferably a human. The term "subject" and "patient" may be used interchangeably.

As used herein the term "isolated" or "purified" in reference to a nucleic acid molecule or a polypeptide refers to a nucleic acid molecule or polypeptide which is separated from the organisms and biological materials (e.g., blood, cells, serum, plasma, saliva, urine, stool, sputum, nasopharyngeal aspirates and so forth), which are present in the natural source of the nucleic acid molecule or polypeptide. An isolated nucleic acid molecule or an isolated polypeptide can also be substantially free of other cellular material, or culture medium when produced by recombinant techniques, or substantially free of chemical precursors or other chemicals when chemically synthesized. Methods of nucleic acid isolation and polypeptide isolation are well known in the art and may include total nucleic acid isolation methods, RNA-specific isolation methods, or DNA-specific isolation methods, affinity purification methods, gel purification methods, antibody purification methods, etc.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin which may be single-stranded or double-stranded and may represent the sense or the antisense strand.

An oligonucleotide is a nucleic acid that includes at least two nucleotides. An oligonucleotide may be designed to function as a "primer." A "primer" is a short nucleic acid, usually a single-stranded DNA oligonucleotide, which may be annealed to a target polynucleotide by complementary base-pairing. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which is used to detect identical, allelic or related nucleic acid sequences. Probes may include oligonucleotides which have been attached to a detectable label or reporter molecule. Typical labels include fluorescent dyes, quenchers, radioactive isotopes, ligands, scintillation agents, chemiluminescent agents, and enzymes.

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC.

A "mutation," or "mutant," or "variant" is meant to encompass at least a single nucleotide variation in a nucleic acid sequence relative to the normal sequence or wild-type sequence. A mutation or may include a substitution, a deletion, an inversion or an insertion of a nucleotide compared to the normal or wild-type sequence. In some embodiments, such variants are naturally occurring (e.g., are first identified in a subject or patient). In other embodiments, such variants are created recombinantly. By way of example, but not by way of limitation, in some embodiments, nucleic acid variants include between 1 and 5 nucleotide differences (e.g., insertions, deletions, substitutions, inversion) as compared to the wild-type sequence. In other embodiments, nucleic acid variants include between 5 and 10 nucleotide differences as compared to the wild-type sequence. In still other embodiments, nucleic acid variants include between 10 and 50 nucleotide differences as compared to the wild-type sequence. In further exemplary embodiments, a nucleic acid variant includes between 50 and 200 differences as compared to the wild-type sequence.

With respect to an encoded polypeptide, a mutation may be "silent" and result in no change in the encoded polypeptide sequence. As is known in the art, the same amino acids may be encoded by a variety of different codons (i.e., a set of three nucleotides). Thus, multiple nucleic acid sequences may encode the same amino acid sequence—such nucleic acid mutants or variants may be characterized as "due to the degeneracy of the genetic code."

A mutation may also result in a change in the encoded polypeptide sequence. Such a change may be a frameshift, a deletion an insertion or a substitution. Amino acid substitutions may be conservative or non-conservative.

As used herein, a "conservative amino acid substitution" is one in which the replacement amino acid has similar chemical properties and/or structure to the original amino acid. A "non-conservative amino acid substitution" is one in which the replacement amino acid differs from the original amino acid in chemical property and/or structure.

Amino acids may be divided according to the chemical properties of their side chains into four basic groups: acidic, basic, uncharged polar and non-polar. By way of example, but not by way of limitation, acidic amino acids may include aspartic acid and glutamic acid; basic amino acids may include lysine, arginine and histidine; uncharged polar amino acids may include glycine, asparagine, glutamine, serine, and threonine; non-polar amino acids may include alanine, valine, leucine, isoleucine, proline, phenylalanine, cysteine, methionine, tyrosine and tryptophan. In general, substitutions between amino acids in the same group may be considered conservative while substitutions between amino acids in different groups may be considered non-conservative. However, the following substitutions between pairs of non-polar amino acids may also be considered conservative substitutions: glycine and alanine; cysteine and serine.

Exemplary, non-limiting examples of regions of PIPKIγ 700 and PIPKIγ 707 that are less likely to tolerate amino acid variation and maintain wild-type protein function include the C-terminus of SEQ ID NO: 3 and SEQ ID NO: 4 (e.g., SEQ ID NOs: 6 and 8), as the C-terminal sequences of each splice variant likely mediate the association with other proteins. Another exemplary regions less likely to tolerate amino acid mutations includes the kinase domains of SEQ ID NO: 3 and 4. Exemplary, non-limiting examples of regions of PIPKIγ 700 and PIPKIγ 707 that are more likely to tolerate amino acid sequence variation and maintain wild-type protein function include portions of the N-terminus of SEQ ID NO: 3 and SEQ ID NO: 4 that are not highly conserved between PIPKIγ, PIPKIα and PIPKIβ isoforms.

As used herein the terms "peptide," "polypeptide" and "protein" are used interchangeably, and are understood to mean a molecule comprising two or more amino acids, where the alpha carboxyl group of one is bound to the alpha amino group of another. A peptide may have a C-terminus and an N-terminus, which relate to the carboxy portion of an amino acid on one end of the peptide chain and the amino portion of an amino acid on the other end of the peptide chain.

When referring to a polypeptide, the terms "C-terminus," "COOH end," "COOH terminus," and "carboxy terminus" may be used interchangeably and include the carboxy portion of a polypeptide chain. Such a portion may include only one or a few amino acids from the C-terminus of the peptide, or may include up to one-fourth, one-third, one-half or more of the length of the polypeptide which includes the C-terminus. Similarly, the terms "N-terminus," "NH2 end," and "amino terminus," may be used interchangeably and includes the amino portion of a polypeptide chain. Such a portion may include only one or a few amino acids from the N-terminus of the peptide, or may include up to one-fourth, one-third, one-half or more of the length of the polypeptide which includes the N-terminus. An exemplary COOH-terminus comprises amino acids 639-700 of the PIPKIγ 700 amino acid sequence (see e.g., FIG. 1), or amino acids 639-707 of PIPKIγ 707 (see e.g., FIG. 1). An exemplary N-terminus may include amino acids 1-639 of SEQ ID NO: 3 (PIPKIγ 700) or amino acids 1-639 of SEQ ID NO: 4 (PIPKIγ 707).

The term "protein domain" includes structurally and/or functionally defined regions of proteins. Proteins may have multiple domains; by way of example but not by way of limitation, domains may include intracellular targeting domains, protein-protein binding domains and kinase domains.

The term "fragment" when used with respect to a polypeptide means a polypeptide derived from a full-length amino acid sequence, such as the PIIPKIγ 707 or PIIPKIγ 700 peptides (e.g., SEQ ID NOS: 3 and 4) having a length less than the full-length polypeptide from which it has been derived. In some embodiments, the fragment is at least about 40%, at least about 50%, at least about 60%, at least about 70%, at least about 80%, at least about 90%, at least about 95%, or at least about 98% or at least about 99% of the length of the full length polypeptide. In other embodiments, a fragment includes at least 5 contiguous amino acids of the full length sequence. In still other embodiments a fragment includes at least 10 contiguous amino acids of the full length sequence. In further embodiments, a fragment includes at least about 15, at least about 20, at least about 25, at least about 30, at least about 35, at least about 40, at least about 45, at least about 50 or at from between about 50 to about 100 contiguous amino acids of the full length sequence. In some embodiments, a polypeptide fragment includes a contiguous stretch of amino acids which uniquely identifies or distinguishes that polypeptide from other polypeptides having a similar amino acid sequence. By way of example but not by way of limitation, the amino acid fragments shown in FIG. 1 distinguish each of the PIPKIγ splice variants from the others.

The term "fragment" when used with respect to a polynucleotide means a polynucleotide derived from a full-length nucleic acid sequence, such as the PIIPKIγ 707 or PIIPKIγ 700 peptides (e.g., SEQ ID NOS: 1 and 2) having a length less than the full-length polynucleotide from which it has been derived. In some embodiments, the fragment is at least about 40%, at least about 50%, at least about 60%, at least about 70%, at least about 80%, at least about 90%, at least about 95%, or at least about 98% or at least about 99% of the length of the full length polynucleotide. In other embodiments, a fragment includes at least 5 contiguous nucleotides of the full length sequence. In still other embodiments a fragment includes at least 10 contiguous nucleotides of the full length sequence. In further embodiments, a fragment includes at least about 15, at least about 20, at least about 25, at least about 30, at least about 35, at least about 40, at least about 45, at least about 50 or at from between about 50 to about 100 contiguous nucleotides of the full length sequence. In some embodiments, a polynucleotide fragment includes a contiguous stretch of nucleotides which uniquely identifies or distinguishes that polynucleotide from other polynucleotides having a similar nucleic acid sequence. SEQ ID NO: 5 and 7 provide non-limiting, exemplary embodiments of nucleic acid fragments.

As used herein, the term "functional fragment" includes portions of a peptide which maintain at least one of the functions of the entire peptide. Such functions include, but are not limited to intracellular targeting, protein-protein interactions, enzyme activity, nucleic acid recognition and binding. Exemplary functional fragments may include the COOH-terminus amino acids (e.g., amino acids 639-700 or 639-707, see FIG. 1) of the PIIPKIγ 707 and PIIPKIγ 700 peptides respectively. These fragments function to target the peptide to a particular subcellular location. Another example of a functional fragment includes amino acids 103-444 of PIPKIγ707 or PIPKIγ700 as shown in SEQ ID NO: 3 or 4. These fragments exhibit lipid kinase function.

In some embodiments, a functional fragment of PIPKIγ 700, PIPKIγ 707, LMO4 or SNX5 may encompass derivatives, homologues, orthologs and analogues of those polypeptides including any single or multiple amino acid additions, substitutions, and/or deletions occurring internally or at the amino or carboxy termini thereof so long as at least one functional activity (e.g., kinase activity, protein binding activity, etc.) remains. For example, when detecting the binding of PIPKIγ 700 to LMO4, an LMO4 protein may include a full-length LMO4 (SEQ ID NO: 10) or any fragment which binds to PIPKIγ 700. When detecting the binding of PIPKIγ 707 to SNX5, an SNX5 protein may include a full-length SNX5 (SEQ ID NO: 9) or any fragment which binds to PIPKIγ 707. The converse may also apply; that is, a fragment of a PIPKIγ splice variant may be used to detect binding to another protein, such as SNX5 or LMO4. By way of example but not by way of limitation, such a fragment may encompass amino acid residues 639-700 of PIPKIγ 700 (amino acids 639-700 of SEQ ID NO:3), which binds LMO4, or amino acid residues 639-707 of PIPKIγ 707 (amino acids 639-707 of SEQ ID NO:4) which bind SNX5. A PIPKIγ 700, 707, LMO4 or SNX5 protein or fragment thereof may be derived from the native polypeptide sequence, recombinantly-produced or chemically-synthesized.

As used herein, the term "PIPKIγ 700" or "700 splice variant" refers to a PIPKIγ splice variant which is exemplified by SEQ ID NO: 1 and 3. "PIPKIγ 700" encompasses natural or artificial variants, homologues, and fragments of the sequences shown in SEQ ID NO: 1 and 3.

As used herein, the term "homolog" refers to a gene related to a second gene by descent from a common ancestral DNA sequence, and encompasses the relationship between genes separated by the event of speciation (e.g., orthologs) and the relationship between genes separated by the event of genetic duplication (e.g., paralogs).

As used herein, the term "PIPKIγ 707" or "707 splice variant" refers to a PIPKIγ splice variant which is exemplified by SEQ ID NO: 2 and 4. "PIPKIγ 707" encompasses natural or artificial variants, homologues, and fragments of the sequences shown in SEQ ID NO: 2 and 4.

The term "having at least about 95% sequence identity" with reference to a nucleic acid sequence is meant to include a nucleic acid molecule which is about 95% or from about 95% to 100% identical to a reference sequence. Exemplary reference sequences include SEQ ID NOS: 1, 2, 5 and 7. With reference to an amino acid sequence, the term "having at least about 95% sequence identity" is meant to include a polypeptide sequence which is about 95% or from about 95% to 100% identical to a reference sequence. Exemplary reference sequences include SEQ ID NOS: 3, 4, 6 and 8.

By "recombinant" is meant that a protein, such as PIP kinase is not produced by naturally-occurring nucleic acid but rather by a "recombinant nucleic acid," that is, one that has been manipulated by one or more procedures to position that nucleic acid either within a vector or at a location in a genome in which it does not naturally occur. The recombinant protein may also be produced in a cell in which it does not naturally occur, purified after its production, and thus separated (e.g., purified) from contaminants such as cells, enzymes, other proteins, nucleic acids, etc.

As used herein, the term "antibody" includes monoclonal and polyclonal antibodies. Such an antibody can belong to any antibody class (IgG, IgM, IgA, etc.). The term "antibody" also includes intact molecules as well as fragments thereof, such as Fab, F(ab')2, Fv, and single chain antibodies which are capable of binding the epitopic determinant. Such antibody fragments retain the ability to selectively bind with the antigen. In some embodiments, the antibodies are humanized. Antibodies described herein also include chimeric antibodies. In some embodiments, antibodies are made which specifically bind to the polypeptides described herein, fragments of these polypeptides, and chimeric fusions including the polypeptides or polypeptide fragments.

As used herein, the term "epitope" includes any antigenic determinant on an antigen to which the antibody binds. Exemplary epitopic determinants include, without limitation, chemically active surface groupings of molecules such as amino acids or sugar side chains. Epitopic determinants usually have specific three dimensional structural characteristics, as well as specific charge characteristics.

As used herein the term "lipid kinase" includes enzymes that are capable of catalyzing the transfer of the terminal phosphate group from ATP to a phospholipid substrate. Exemplary substrates include PI4P; a lipid kinase will be capable of transferring a terminal phosphate to the substrate, yielding, in this example, PI4,5$P_2$.

The term "lipid kinase activity" includes the enzymatic activity of and ability to phosphorylate a phospholipid substrate. A lipid kinase activity may be enhanced (e.g., the lipid kinase activity of a given kinase may show increased activity, processivity or both) as compared to another kinase or the same kinase under different conditions. Or, a lipid kinase activity may be "inhibited" or "reduced" as compared to another kinase, or the same kinase under different conditions. Lipid kinase activity can be measured by methods known in the art and described in the examples herein.

I. Examples

The following examples and discussion are provided to aid the reader in understanding the novel PIPKIγ 700 and PIPKIγ 707 splice variants, and are not intended to be limiting. Those skilled in the art will understand that in some instances, methods, procedures, reagents, etc. may be substituted with others which will provide the same or similar results.

A. Methods for Identification, Isolation and Production of Novel PIP Kinases

The PIPKIγ700 and PIPKIγ707 DNA was isolated from MCFI10-A human breast epithelial cell cDNA via PCR using the forward primer 5'-ATGGAGCTGGAGGTACCGGA-3' (SEQ ID NO: 13) and the reverse primer 5'-TTACCCAAAGCCCTTCTGGAAA-3' (SEQ ID NO: 14). The coding regions of PIPKIγ700 and PIPKIγ707 were subcloned into the pCMV-HA vector (Clontech) for mammalian expression or the pET28 vector (Novagen) for expression in *E. coli*. Purification of recombinant, kinase active PIPKIγ700 and PIPKIγ707 from *E. coli* was accomplished using standard 6-histidine nickel affinity chromatography.

Figure 2:
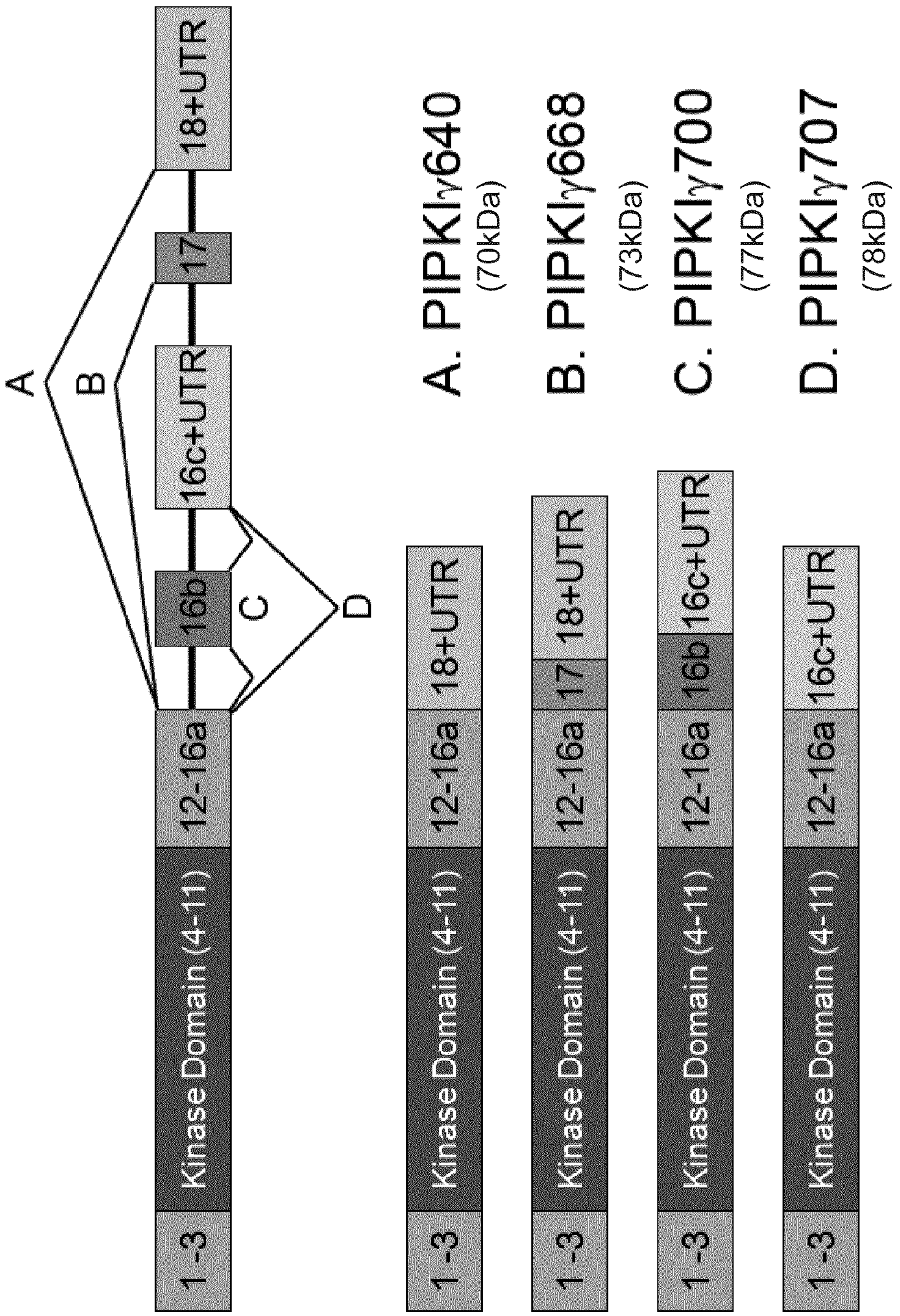
FIG. 2 shows a schematic representation of the PIPKIγ splice variant exons and domains.
Figure 3:
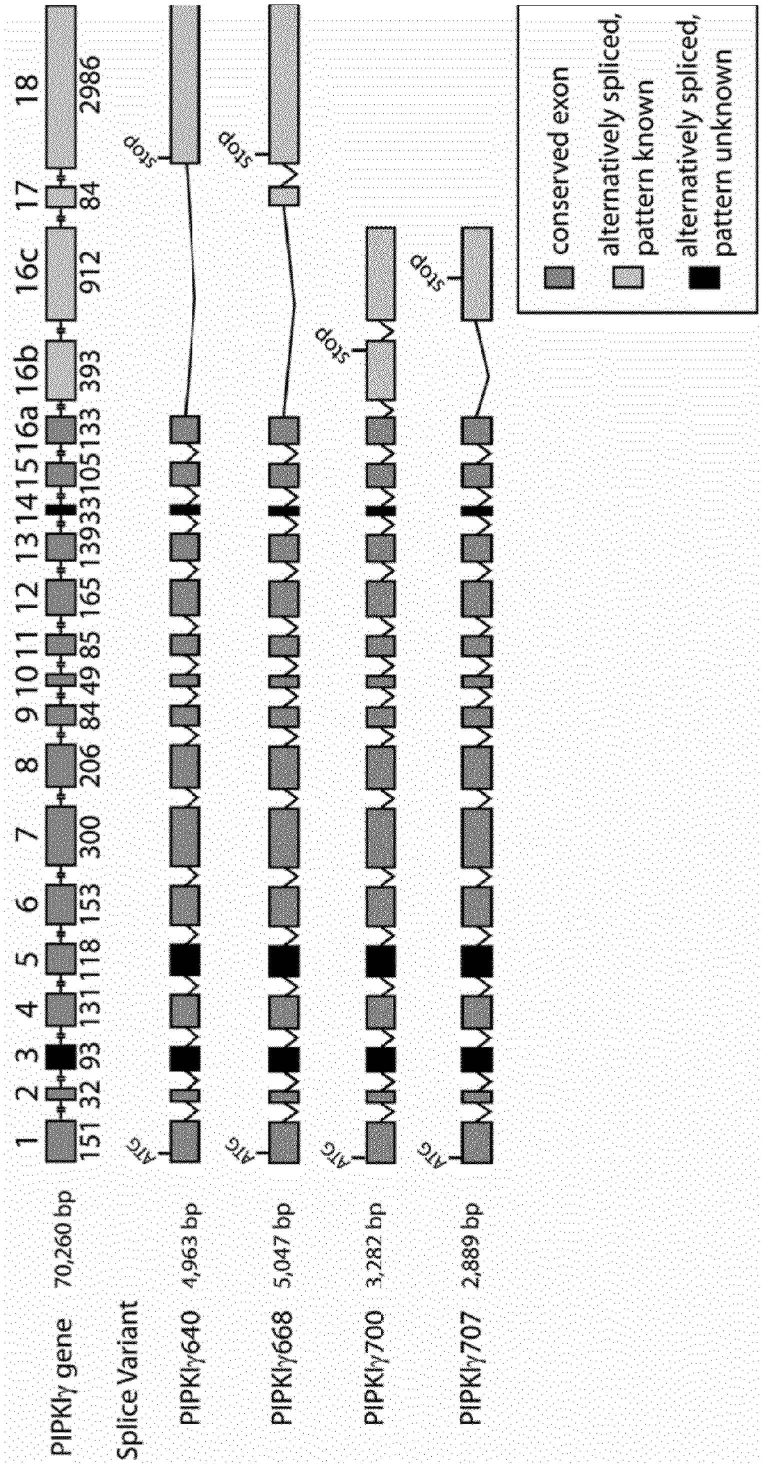
FIG. 3 shows a schematic representation of the PIPKIγ splice variant exon structure.

A schematic exon map of the human PIPKIγ splice variants, PIPKIγ 640, 668 and novel splice variants PIPKIγ 700 and 707 is shown in FIGS. 2 and 3. The newly identified splice variants include exons not found in PIPKIγ 640 and PIPKIγ 668. As shown in FIGS. 2 and 3, PIPKIγ 700 includes exons 16b and 16c, while PIPKIγ 707 includes exon 16c. An amino acid alignment of the unique C-terminal sequence of the PIPKIγ splice variants is shown in FIG. 1.

B. Kinase Activity Assay

Figure 14:
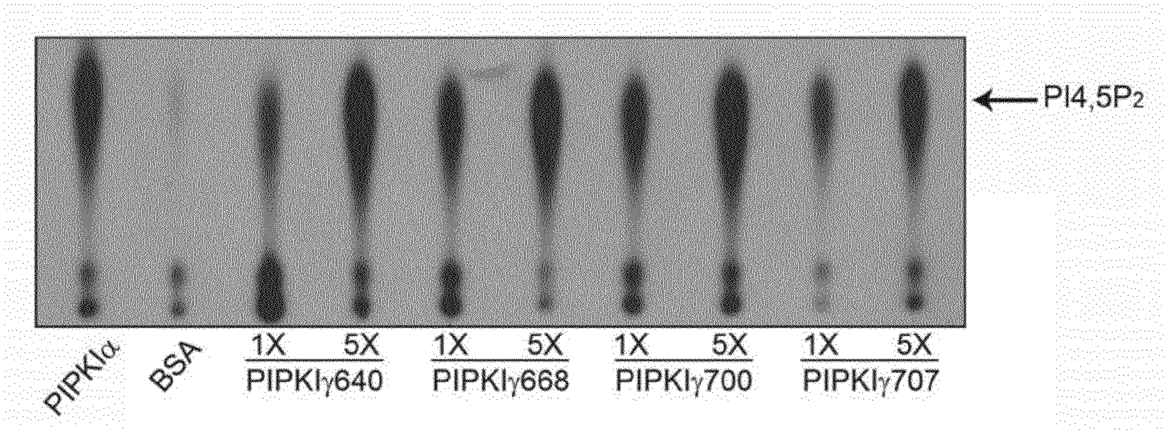
FIG. 14 shows a lipid kinase assay demonstrating that PIPKIγ 700 and PIPKIγ 707 possess PI4P 5-kinase activity.

Methods known in the art were used to test the novel splice variants for kinase activity (see e.g., Ling, et al. (2002) Nature 420:89-93). Briefly, experiments were performed in which PI4P micelles or Folch brain extracts were used as a substrate for phosphorylation by recombinant PIPKIγ 700 and PIPKIγ 707 splice variants. Labeled 32P-γATP was used in the reactions to monitor phosphorylation when different amounts of purified PIPKIγ 700 or PIPKIγ 707 protein were added. Labeled phosphorylation products were observed by thin layer chromatography. It was found that both variants possess kinase activity (FIG. 14).

Figure 15:
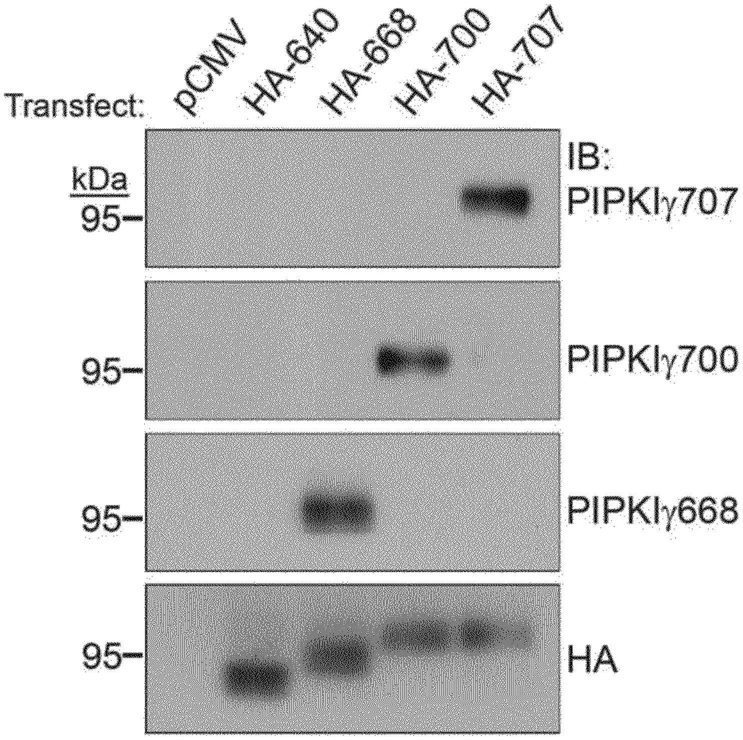
FIG. 15 shows the specificity of the PIPKIγ 700 and PIPKIγ 707 polyclonal antibodies in the detection of ectopically expressed HA-PIPKIγ splice variants.
Figure 16:
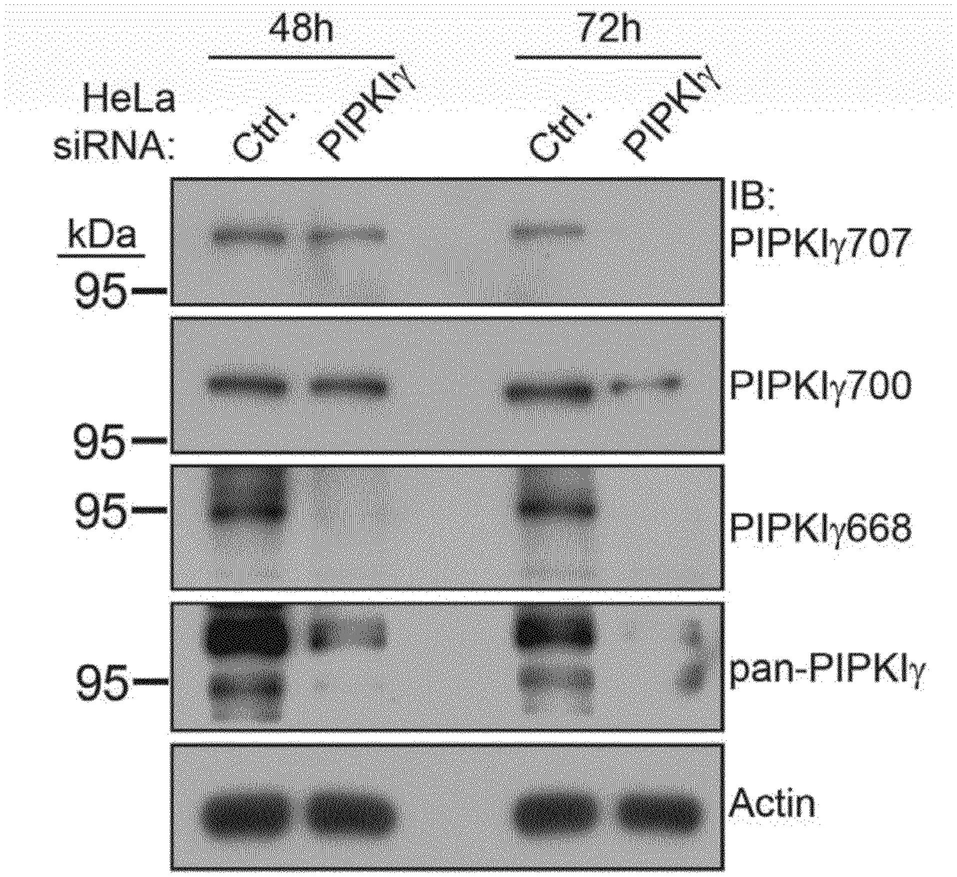
FIG. 16 depicts a western blot of endogenous PIPKIγ splice variants from HeLa cells before and after siRNA-mediated knockdown of total cellular PIPKIγ.

C. Assays to Determine the Relative Amounts of the Novel Variants and Subcellular Localization Method well known in the art can be used to generate antibodies specific to each of the novel splice variants. One such method is described below. Briefly, antibodies specific to PIPKIγ 700 and PIPKIγ 707 were generated by immunizing rabbits with each unique C-terminal sequence (SEQ ID NOS: 6 and 8, respectively) conjugated to keyhole limpet hemocyanin. The antisera was then purified over affinity columns for the PIPKIγ 700 or PIPKIγ 707 C-terminal sequence. Each antibody specifically detected its targeted splice variant with no detectable cross reactivity towards other PIPKIγ splice variants. (FIG. 15). Verification of specificity for each PIPKIγ splice variant was also determined by western blotting of HeLa cell lysates in which total cellular PIPKIγ had been knocked down using siRNA (FIG. 16).

Experiments using these antibodies showed that in most cell lines, both PIPKIγ 700 and PIPKIγ 707 protein are present in lower amounts than PIPKIγ 668 protein.

Figure 17:
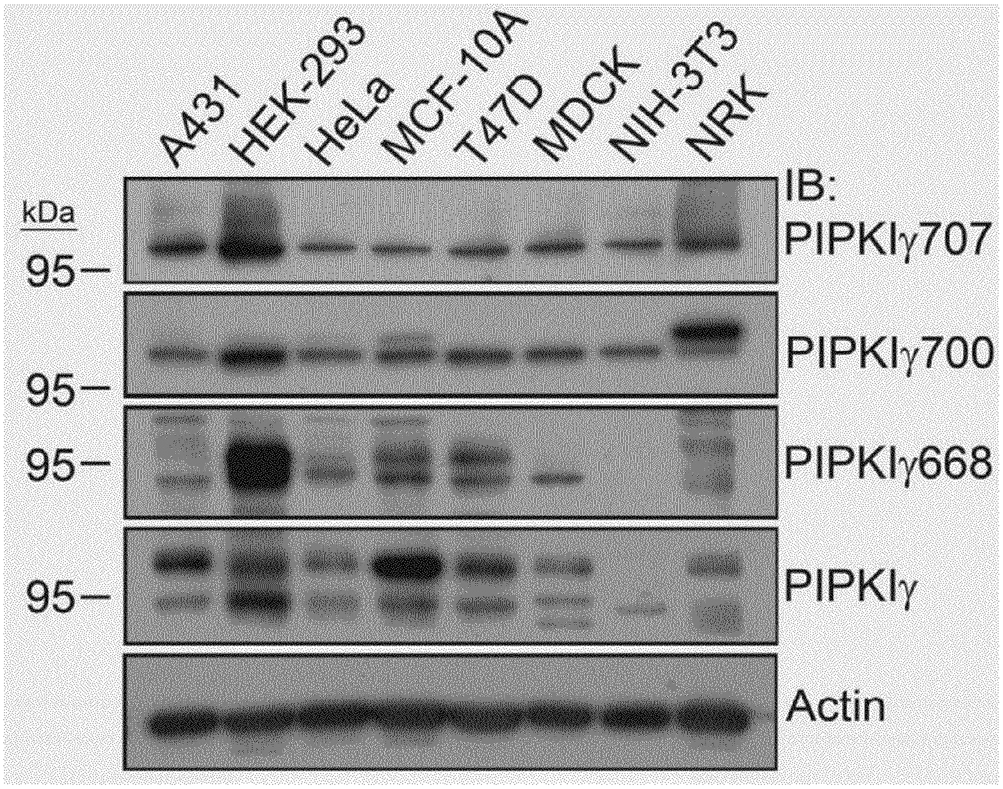
FIG. 17 shows a western blot of PIPKIγ splice variants from multiple human, mouse, rat, and dog cell line lysates.

Western blotting of A431, HEK-293, HeLa, MCF10A, T47D, and MDCK cells indicate that PIPKIγ 668 is present in greater amounts than either PIPKIγ 700 or PIPKIγ 707. However, PIPKIγ 700 and PIPKIγ 707 are present in greater amounts than PIPKIγ 668 in NIH-3T3 and NRK cells (FIG. 17). The sub-cellular localization of each splice variant was determined by creating and detecting HA-PIPKIγ 700 and HA-PIPKIγ 707 fusions ("HA-700" and "HA-707") using methods well known in the art (see e.g., Ling, et al. (2002) Nature 420:89-93).

Figure 4:
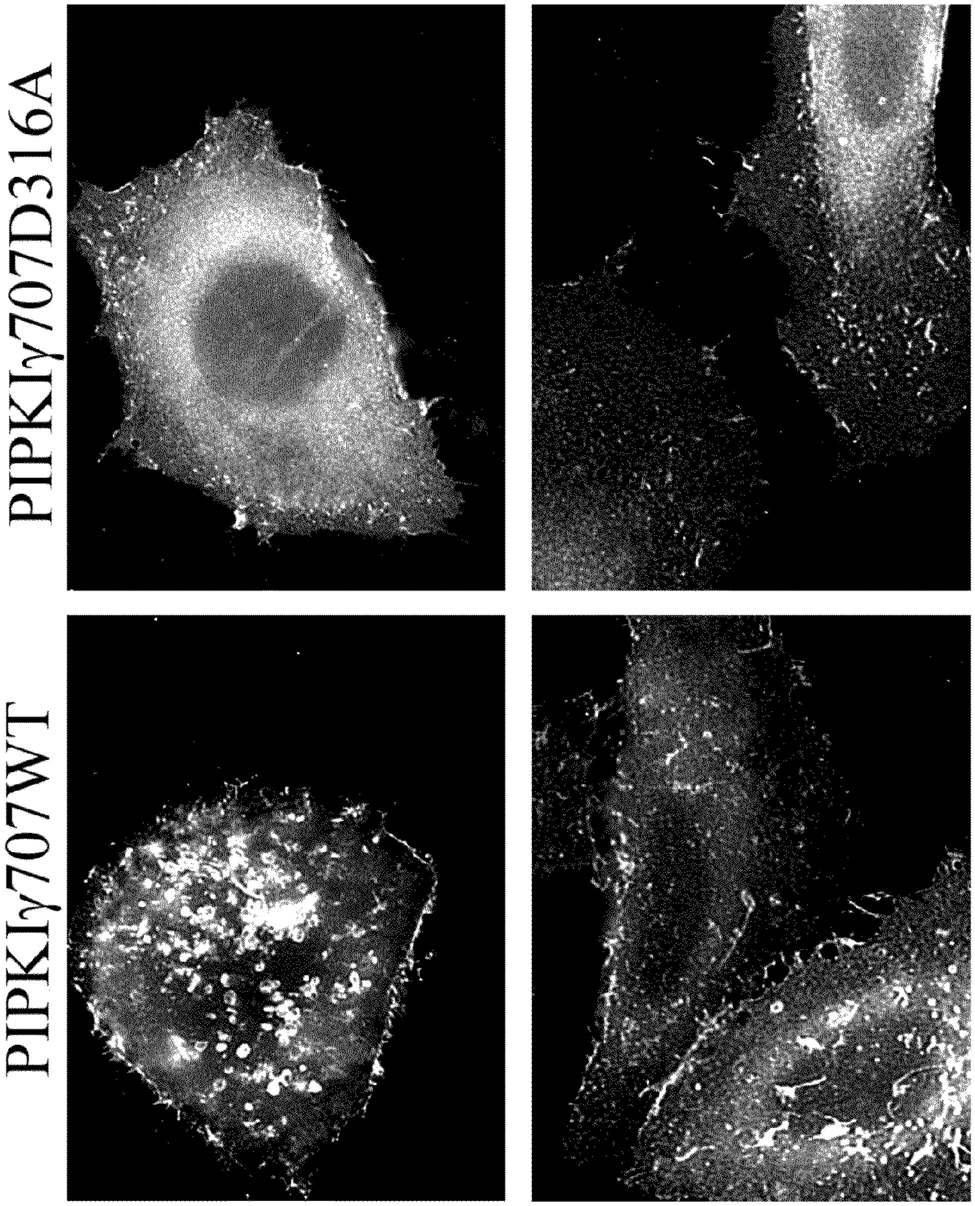
FIG. 4 shows the subcellular localization of PIPKIγ 707 in the PIPKIγ 707 wild-type and PIPKIγ 707 D316A mutant.

Both HA-700 and HA-707 appeared to display distinct subcellular targeting patterns. HA-700 and HA-707 were ectopically expressed in HeLa cells, and as shown in FIG. 4, the HA-707 variant appears to localize to punctuate membrane associated structures and also tubular and vesicular structures located in the cytosol. Additionally, PIPKIγ 707 kinase activity appears to be required for proper subcellular localization. When a D316A mutation was made to the catalytic core, the localization of the mutant PIPKIγ 707 became mostly diffuse and cytosolic. (See FIG. 4). However a small portion of the PIPKIγ 707 D316A mutant did appear at smaller punctate structures at the plasma membrane in some cells (bottom right of FIG. 4).

Figure 5:
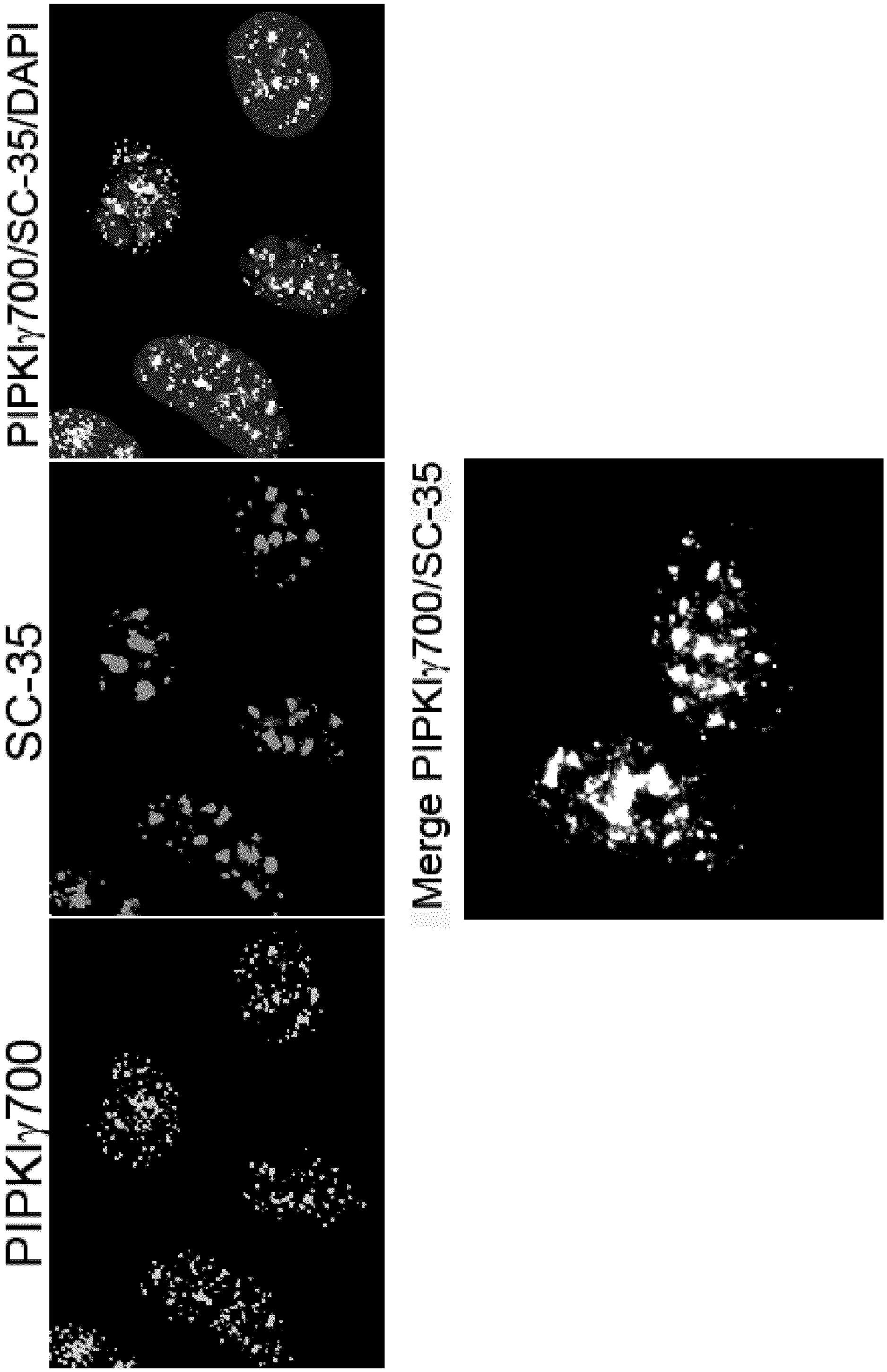
FIG. 5 shows the subcellular localization of PIPKIγ 700 in the nucleus. SC35, a nuclear marker, and DAPI labeled DNA are also visualized.

PIPKIγ 700 is a nuclear localized phosphoinositide kinase. To characterize PIPKIγ 700 subcellular localization, human breast epithelial MCF-10A cells where stained with PIPKIγ 700, SC35 (nuclear marker) antibodies, and DAPI for DNA. Results are shown in FIG. 5. Cells were grown on glass coverslips overnight, washed, and subjected to fixation with chilled methanol for 10 minutes. Cells were then stained with either antibodies towards PIPKIγ700 (green, top left), or SC35 (red, top center) and DAPI (blue, top right shows all three merged). Coverslips were mounted on glass slides and imaged on a Nikon TE-2000U equipped with Metamorph imaging software. Images were analyzed for colocalization by color overlay. The bottom image is a higher resolution color overlay.

D. Interaction of PIPKIγ 700 and 707 with Other Proteins

Numerous screening methods are known in the art to identify protein-protein interactions. Two exemplary methods, the yeast two-hybrid screen and co-immunoprecipitation, were used to identify proteins which interact directly with the PIPKIγ 700 and PIPKIγ 707 splice variants. Other exemplary methods include pull-down assays, gel shift analysis, western blot analysis and ELISA analysis.

1. PIPKIγ 707 and SNX5

To identify proteins which may interact with (e.g., bind to) the 707 splice variant, a yeast two-hybrid screen was performed according to methods known in the art (e.g., James et al., (1996) Genetics 144:1425-1436). Using the C-terminus of the 707 splice variant as bait (SEQ ID NO: 8), an interaction with sorting nexin 5 ("SNX5") was identified.

Sorting nexins, a family of about 30 hydrophilic, membrane-associated and cytoplasmic proteins, play a role in protein sorting, targeting, and endocytosis. All include a loosely homologous phosphoinositide-binding domain. The phosphoinositide-binding domain of SNX5 has been show to bind PI3P as well as PI4,5$P_2$, the second messenger generated by PIPKIγ isoforms, including PIPKIγ 707.

Figure 6:
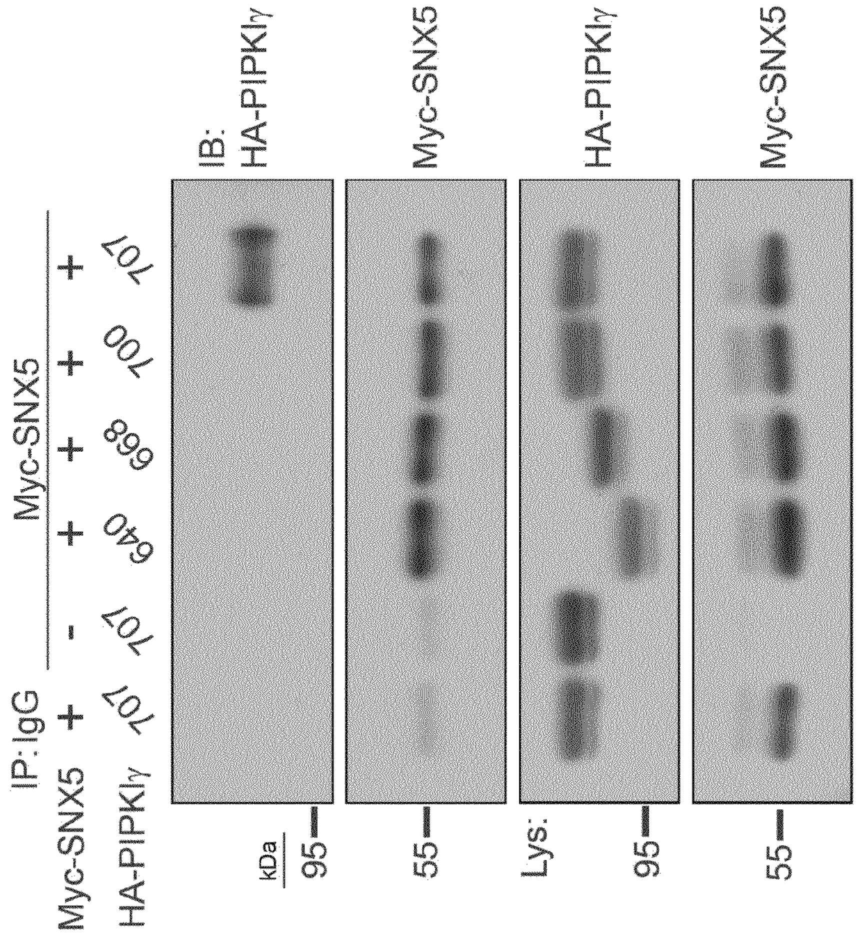
FIG. 6 shows experimental results of a co-immunoprecipitation assay. The results demonstrate an interaction between SNX5 and PIPKIγ 707.
Figure 7:
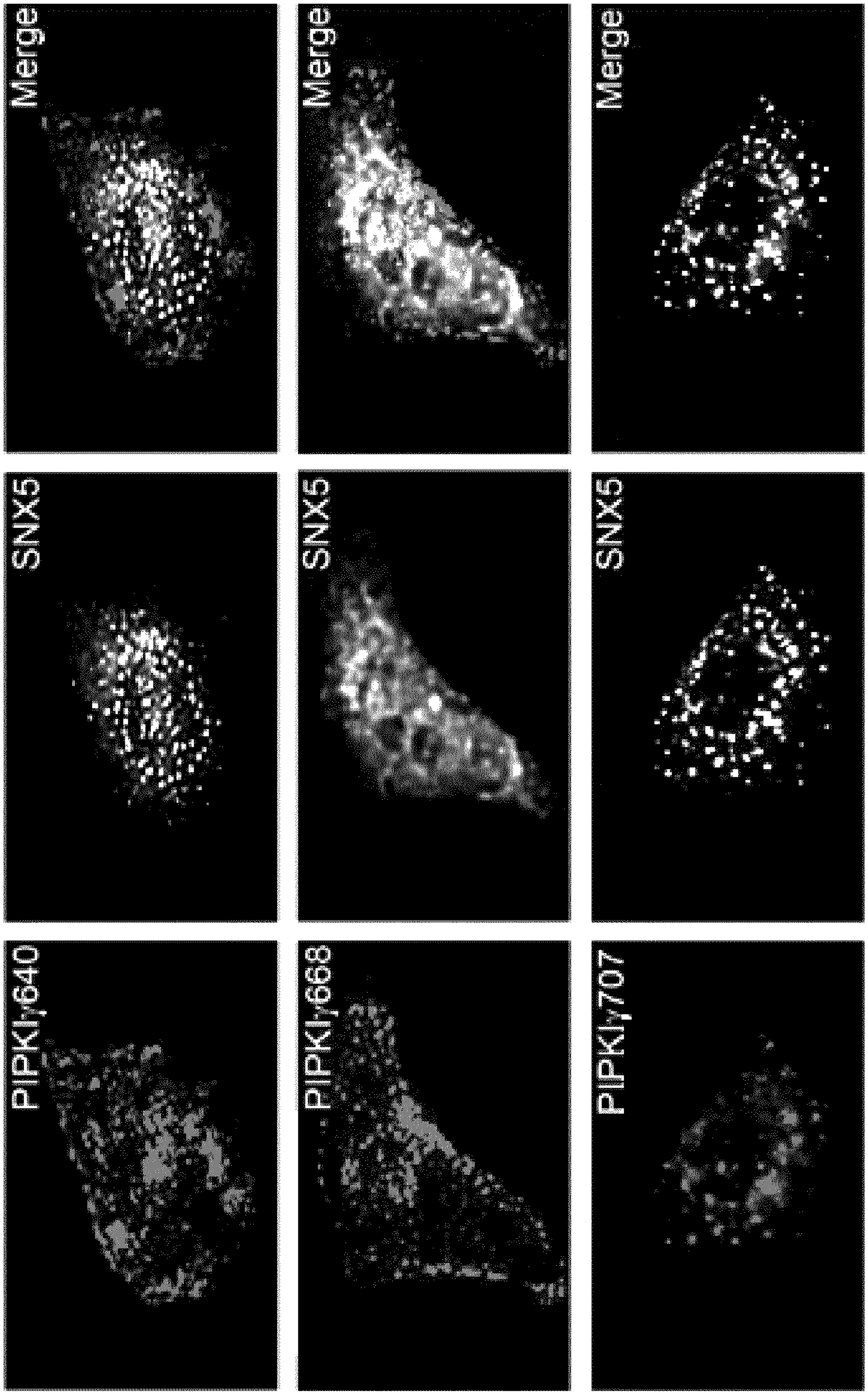
FIG. 7 shows the co-localization of Myc-SNX5 and HA-PIPKIγ 707 inside HeLa cells.

The specificity of the interaction between PIPKIγ 707 and SNX5 was confirmed in vivo via co-immunoprecipitation using methods known in the art (see e.g., Ling, et al. (2002) supra; Towler, et al. (2004) Molecular Biology of the Cell. Vol. 15, Issue 7, 3181-3195) (see FIG. 6). The interaction between SNX5 and PIPKIγ 707 was further characterized using antibodies specific for the PIPKIγ 707 variant and specific for SNX5 to demonstrate that PIPKIγ 707 and SNX5 partially co-localize in HeLa cells at punctuate structures near the plasma membrane, and to a lesser extent, in the cytoplasm. Such co-localization is shown in FIG. 7, bottom row. However, the PIPKIγ 640 and 668 isoforms do not co-localize with SNX5, further indicating specificity of the 707 splice variant for this association. Briefly, the different PIPKIγ isoforms were co-expressed in HeLa cells. Human epithelial HeLa cells were transfected with HA-PIPKIγ and grown on glass cover slips overnight, washed, and subjected to fixation with chilled methanol for 10 minutes. Cells were then stained with either antibodies towards pan-PIPKIγ (red, first column) or SNX5 (green, second column). Cover slips were mounted on glass slides and imaged on a Nikon TE-2000U equipped with Metamorph imaging software. Images were analyzed for co-localization by color overlay.

Accordingly, the data supports PIPKIγ 707 as playing a role in regulating SNX5 localization. As such, this splice variant is very likely an important participant in protein sorting, trafficking and endocytosis, and thereby provides a novel therapeutic target for diseases associated with SNX5 dysfunction.

Figure 8:
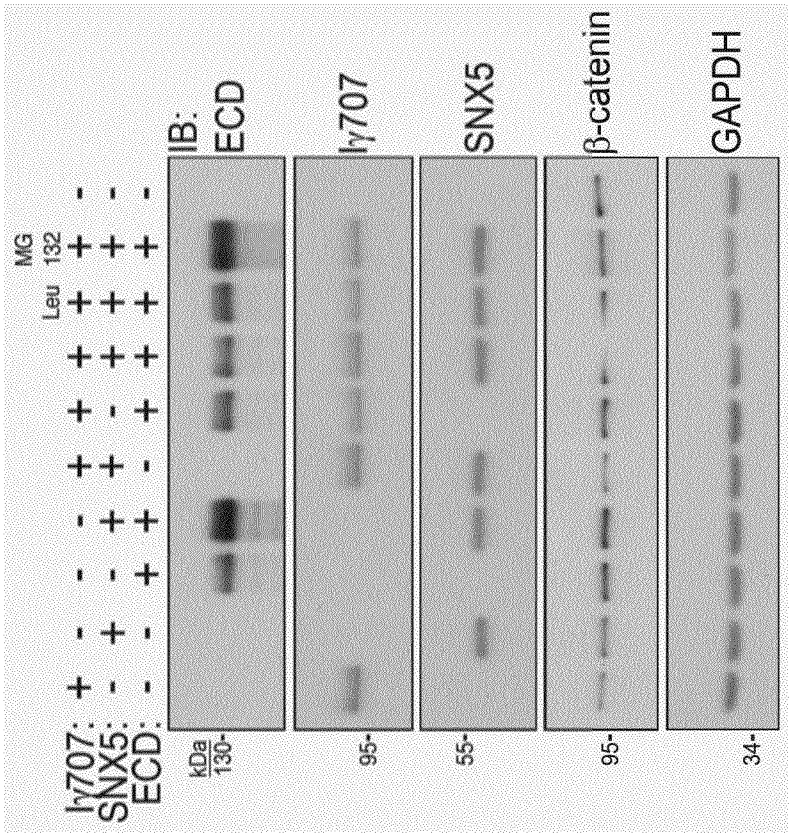
FIG. 8 shows a western blot of the protein content of HeLa cells transfected with PIPKIγ 707, SNX5, E-cadherin or a combination of constructs.

The cellular content of E-cadherin protein is controlled by PIPKIγ 707 and SNX5, as shown in FIG. 8. Experiments were performed as follows. HeLa cells were transfected overnight with the indicated DNA constructs (PIPKIγ 707=γ707; SNX5 and E-cadherin=ECD) at equal ratios. Cells were treated with either 100 ug/ml leupeptin or 10 μM MG-132 for approximately 16 hours at 37° C. where indicated. Cells were then lysed directly into SDS sample buffer, and protein content was quantified with Bradford's reagent. Equal microgram amounts of the whole cell lysates were subjected to Western blotting with the indicated antibodies.

2. PIPKIγ 700 and LMO4

To identify proteins which interact with the PIPKIγ 700 variant, a yeast two-hybrid screen as describe above was performed. Using the C-terminus of the PIPKIγ 700 variant as bait (SEQ ID NO: 6), an interaction with LMO4, a transcription factor and breast cancer marker, was identified. Again, the specificity of this interaction was confirmed in vivo via co-immunoprecipitation as described above. (Data not shown).

LMO4, a member of the Lim-only subclass of LIM domain proteins, is a zinc finger protein which acts to mediate protein-protein interaction in multi-protein complexes. LMO4 has been shown to be over-expressed in a numerous breast cancers, to negatively regulate mammary epithelial differentiation in vitro, and to inhibit BRCA1-mediated transcriptional activity.

Accordingly, the association of PIPKIγ 700 with LMO4 this splice variant is likely playing a fundamental role in breast cancer.

3. PIPKIγ 700 and 707 Interaction with β-Catenin

Figure 9:
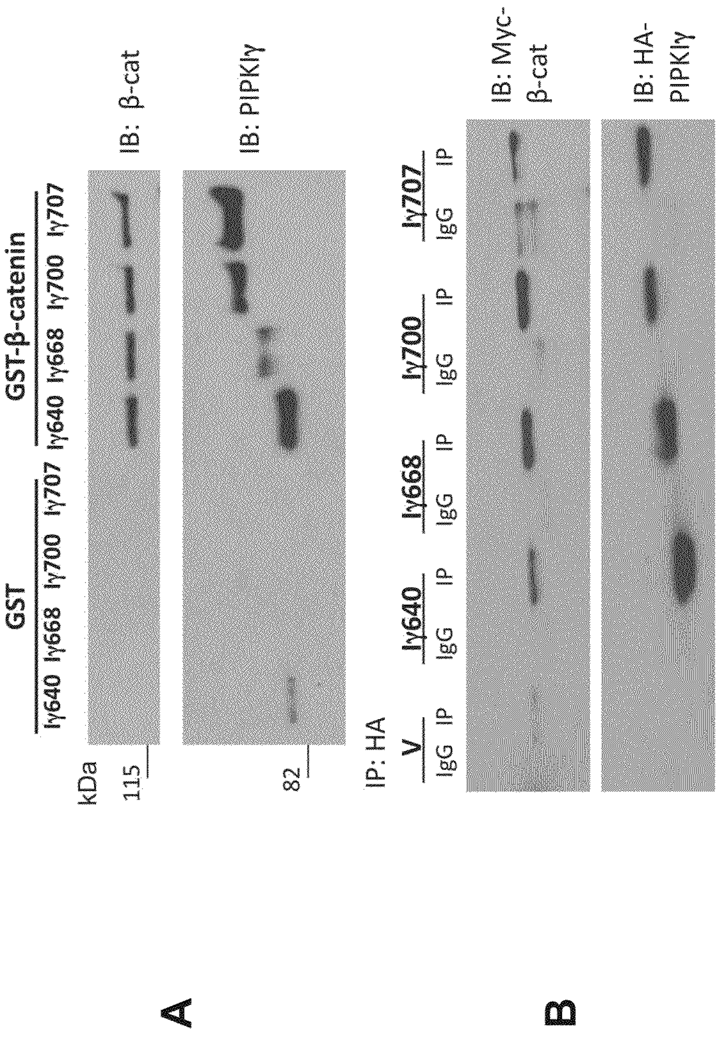
FIG. 9A shows the results of a GST pulldown assay, and illustrates interactions between PIPKIγ isoforms and β-catenin.
FIG. 9B shows the results of an immunoprecipitation and western blot analysis, and illustrates interactions between PIPKIγ isoforms and β-catenin.

PIPKIγ 700, 707 and other PIPKIγ isoforms interact with the oncogene beta-catenin (β-catenin). This interaction was identified using biochemical and proteomic approaches in which PIPKIγ isoforms were immunoprecipitated and β-catenin was shown to form an association. A direct interaction between β-catenin and PIPKIγ 700 and PIPKIγ 707 was demonstrated by GST pull down of the purified proteins. Results are shown in FIG. 9A. Interaction between other PIPKIγ isorforms and β-catenin is also shown is FIG. 9A.

Further, when PIPKIγ isoforms are co-expressed in cultured cells and immunoprecipitated there is a clear association with β-catenin (see FIG. 9B) in vivo. Myc-β-catenin and HA-PIPKIγ isoforms were expressed in A431D, CHOKI cells and HA-PIPKIγ was immunoprecipitated. HA-PIPKIγ was then western blotted for β-catenin.

Figure 10:
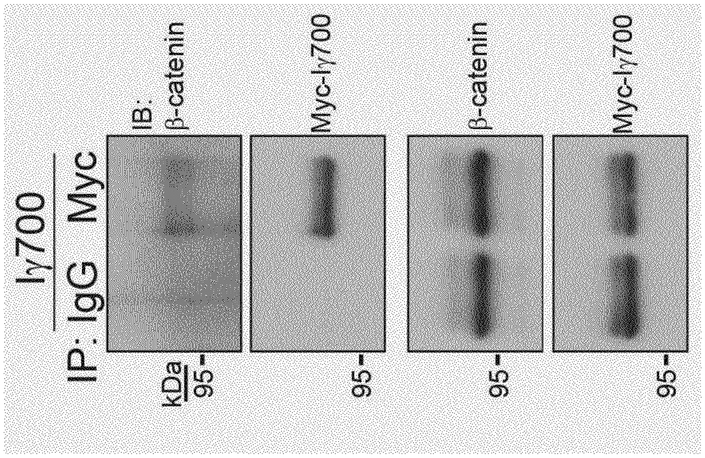
FIG. 10 shows the results of an immunoprecipitation and western blot analysis, and illustrates an interaction between PIPKIγ 700 and β-catenin.

The in vivo β-catenin interaction with PIPKIγ 700 was further characterized. Myc-PIPKIγ 700 was transfected into Hela cells, and cells were incubated overnight. Cells were then lysed in modified RIPA buffer with phosphatase and protease inhibitors and cleared by centrifugation at 4° C. Myc-PIPKIγ 700 complexes were immunoprecipitated from cell lysates overnight at 4° C. and then subjected to western blotting with anti-Myc and anti-β-catenin antibodies. Results are shown in FIG. 10.

β-catenin is a key oncogene in many cancers but in particular plays key roles in the progression of epithelial cancers such as breast cancers. β-catenin is a member of the armadillo family of proteins and has multiple armadillo repeat domain which are specialized for protein-protein binding. Stabilization of the β-catenin protein, either by blocking the destruction complex or re-localizing b-catenin from the membrane to the nucleus, has been demonstrated in certain cancers and leads to the increase in proliferation of related tumors, including breast cancer tumors.

β-catenin interacts with many proteins and each of these interactions regulate β-catenin's function. In epithelial cells β-catenin interacts with E-cadherin and mediates epithelial cell morphogenesis. When not associated with cadherins, β-catenin can associate with other proteins such as TCF/LEF and APC. When β-catenin is targeted to the nucleus, interaction of β-catenin with the TCF family of transcription factors has been shown to regulate gene expression. In addition, the Wnt pathway and other signaling cascades regulate the association of b-catenin with other proteins. The interaction of β-catenin with specific binding partners (such as APC, cadherins, TCF/LEF, transcription factors, a-catenin, ICAT, axin, kinases, ubiquitination machinery, etc.) regulates β-catenin function in controlling cellular proliferation. These interactions are highly regulated by signaling pathways such as protein phosphorylation, proteolysis, and expression of interacting proteins such as E-cadherin. The association between β-catenin and PIPKIγ isoforms indicates a novel mechanism for regulation of β-catenin by the phosphoinositide kinases and phosphoinositide signals. In support, the data described above indicates that PIPKIγ 700 and PIPKIγ 707 are important in the modulation of β-catenin activity in the cytoplasm or in the nucleus.

4. PIPKIγ 700 and PIPKIγ 707 Interaction with HER1, the HGF Receptor (c-MET Oncogene) and Src, all Tyrosine Kinases with Oncogenic Roles Both the PIPKIγ 700 and PIPKIγ 707 splice variants can be regulated by HER1. Although there is no evidence that PIPKIγ 700 or PIPKIγ 707 can be directly regulated by HER1, both of these kinases are tyrosine phosphorylated when cells are stimulated with EGF, and there is strong evidence that the PIPKIγ 668 isoform is directly phosphorylated by the EGF receptor. The residue phosphorylated, tyrosine 639, is present in all PIPKIγ isoforms (see e.g., Sun, et al. *JCB* (2007) supra; Towler et al. (2004) Molecular Biology of the Cell., supra).

Figure 18:
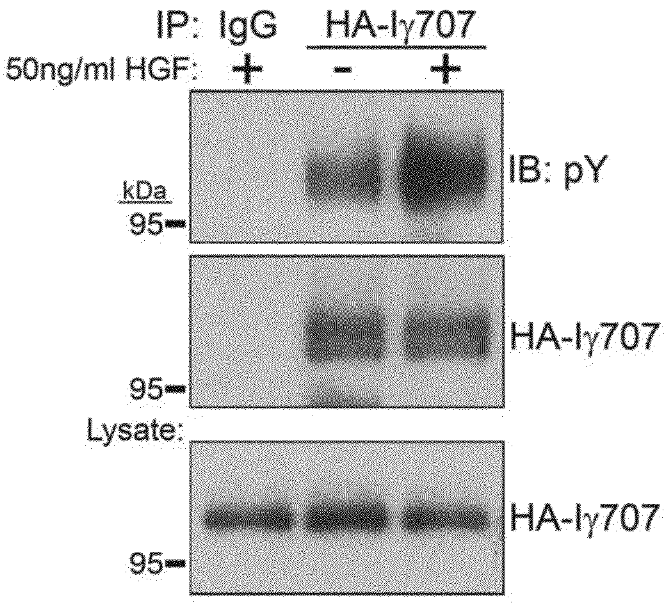
FIG. 18 shows a western blot of HA-PIPKIγ 707 immunoprecipitated from cells treated with human growth factor (HGF). Western blots were performed with anti-HA antibodies and anti-phosphotyrosine antibodies. Cells treated with HGF show a higher amount of phosphorylated PIPKIγ 707.

Hepatocyte growth factor (HGF) stimulation also leads to the tyrosine phosphorylation of PIPKIγ 707. The data for HGF stimulated phosphorylation of PIPKIγ 707 is shown in FIG. 18. Experiments were performed as follows. MDCK cells transfected with HA-PIPKIγ 707 were cultured for approximately 16 hours in 0.1% FBS/DMEM at 37° C. before stimulation with 50 ng/ml hepatocyte growth factor for 5 minutes at 37° C. Cells were lysed via sonication in modified RIPA buffer with phosphatase and protease inhibitors, and cell lysates were cleared by centrifugation at 4° C. HA-PIPKIγ 707 was immunoprecipitated from cell lysates overnight at 4° C. and then subjected to Western blotting with anti-phosphotyrosine and anti-HA antibodies.

PIPKIγ 707 lipid kinase activity is required for its own tyrosine phosphorylation in HeLa cells. This was demonstrated as follows. HeLa cells transfected with WT or kinase inactive (D316A) PIPKIγ 707 were lysed in modified RIPA buffer with phosphatase and protease inhibitors, and cell lysates were cleared by centrifugation at 4° C. Myc-PIPKIγ

707 was immunoprecipitated from cell lysates overnight at 4° C. and then subjected to Western blotting with anti-phosphotyrosine and anti-Myc antibodies. Results are shown in FIG. 19.

The oncogene tyrosine kinase Src is downstream of many growth stimulation pathways and is activated by both EGF and HGF stimulation. Src is known to play key roles in the progression of epithelial cancers.

Figure 19:
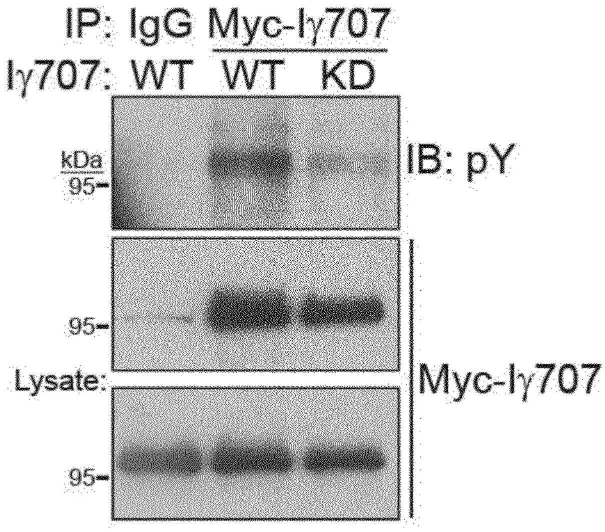
FIG. 19 shows a western blot of Myc-PIPKIγ 707 wild-type or Myc-PIPKIγ 707(D316A) mutant immunoprecipiated from HeLa cells. Western blots were performed with anti-Myc and anti-phosphotyrosine antibodies.
Figure 20:
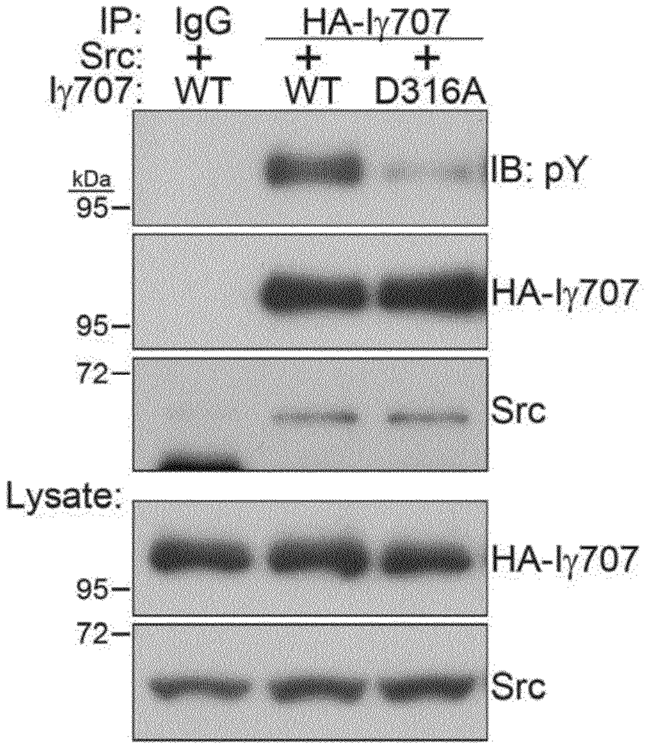
FIG. 20 shows a western blot of HA-PIPKIγ 707, HA-PIPKIγ707(D316A) and Src immunoprecipitated from transfected HeLa cells.

In cells, PIPKIγ 707 is tyrosine phosphorylated and PIPKIγ 707 tyrosine phosphorylation requires PIPKIγ 707 activity (FIG. 19). PIPKIγ 707 (and other PIPKIγ isoforms) serves as a substrate for Src, and Src was observed to associate with PIPKIγ 707 by co-immunoprecipitation. The tyrosine phosphorylation of the PIPKIγ 707 by Src also required active PIPKIγ 707, indicating that the $PI4,5P_2$ generated by PIPKIγ 707 regulates PIPKIγ 707 phosphorylation by Src. Briefly, HeLa cells were co-transfected with WT or kinase inactive (D316A) PIPKIγ 707 and c-Src and cultured overnight at 37° C. Cells were lysed in modified RIPA buffer with phosphatase and protease inhibitors, and cell lysates were cleared by centrifugation at 4° C. HA-PIPKIγ 707 complexes were immunoprecipitated from cell lysates overnight at 4° C. and then subjected to Western blotting with anti-phosphotyrosine and anti-HA, and anti-Src antibodies. Results are shown in FIG. 20.

E. PIPKIγ 700 and PIPKIγ 707 Isoforms as Breast Cancer Markers

Figure 12:
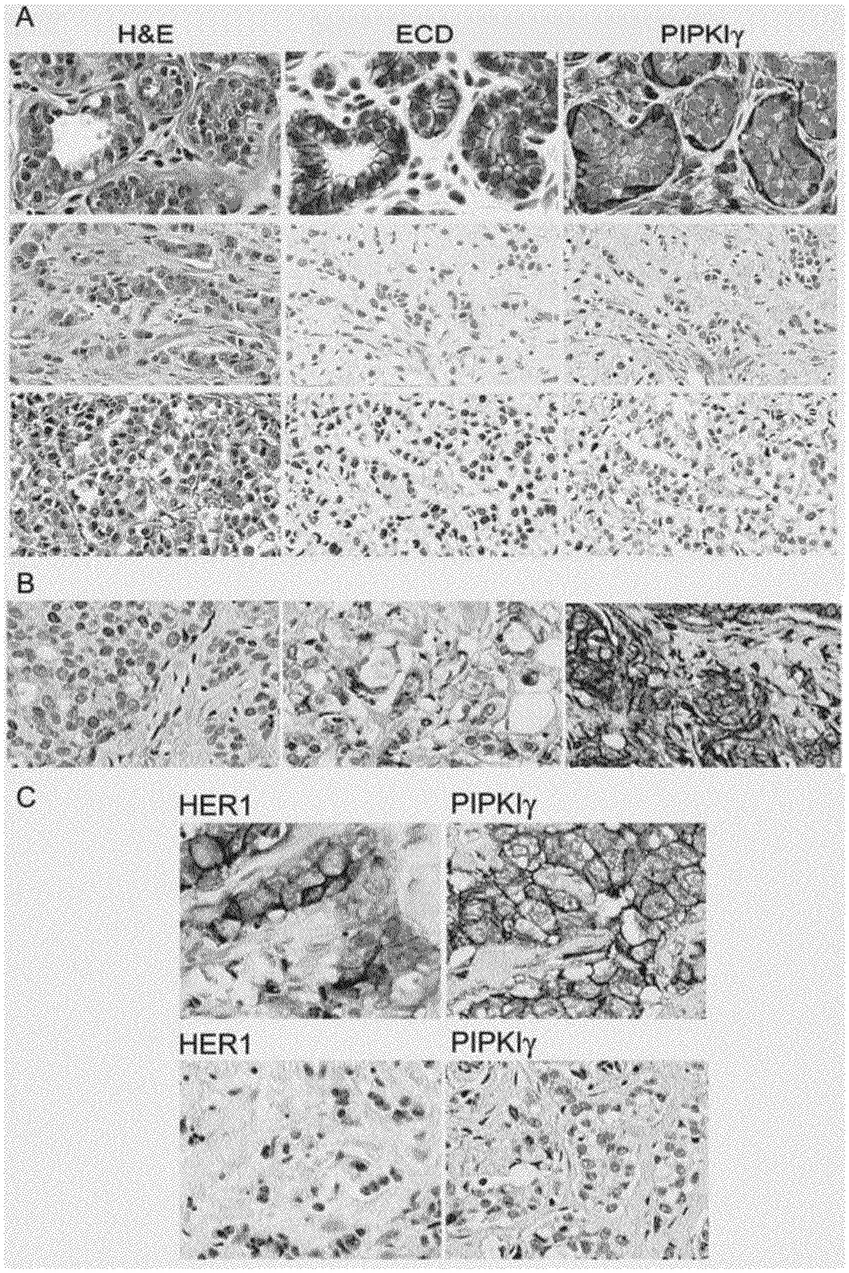
FIG. 12 shows staining of breast cancer tissue with PIPKIγ antibodies. (A) shows hematoxylin and eosin (H&E), E-cadherin and PIPKIγ staining of normal breast tissue (top); breast carcinomas that show a loss of both E-cadherin and membrane PIPKIγ (middle); a fraction of carcinomas that show both a mis-targeting of E-cadherin and a loss of PIPKIγ (bottom). (B) Expression of PIPKIγ in breast carcinomas. Left panel, shows representative breast carcinomas stained negative for PIPKIγ. Middle panel, shows representative breast carcinomas stained weakly positive for PIPKIγ. Right panel, shows representative breast carcinomas stained strong positive for PIPKIγ. (C) Shows representative immunohistochemical staining of breast tumor tissue for HER-1 and PIPKIγ. The top panels show strong expression of HER-1 and PIPKIγ, whereas the bottom shows weak staining for both antigens.

As PIPKIγ is required for normal E-cadherin function, the correlation of E-cadherin and PIPKIγ in normal breast and breast carcinomas was examined using tissue arrays. FIG. 12 shows examples of the tissue array staining patterns. In normal breast tissue, PIPKIγ was observed at the plasma membrane with E-cadherin and PIPKIγ also showing a strong basal cell layer staining (see e.g., FIG. 12A, top row). In over 69% of breast carcinomas where E-cadherin was negative, PIPKIγ was also negative (see e.g., FIG. 12A, middle row). In a small fraction of breast carcinomas where E-cadherin membrane staining was totally lost but was present in or around the nucleus, PIPKIγ showed negative membrane staining (FIG. 12A, bottom row). Table 1 below summarizes the PIPKIγ staining patterns and E-cadherin staining patterns.

TABLE 1

E-cadherin and PIPKIγ staining patterns

| E-cadherin staining pattern | PIPKIγ Staining Pattern: Negative | Cytoplasmic | Weak Mem. | Strong Mem. | Basal Layer | Total |
|---|---|---|---|---|---|---|
| Negative | 36 | 1 | 12 | 3 | 0 | 52 |
| Cytoplasmic | 7 | 0 | 4 | 4 | 0 | 15 |
| Nuclear | 8 | 1 | 2 | 1 | 0 | 12 |
| Nuclear + Mem. | 6 | 0 | 9 | 0 | 1 | 16 |
| Weak Mem. | 42 | 3 | 50 | 22 | 5 | 122 |
| Strong Mem. | 36 | 17 | 64 | 34 | 1 | 152 |
| Total | 135 | 22 | 141 | 64 | 7 | 369 |

When the tissue array data were analyzed, a highly significant correlation between membranous E-cadherin (either strong or weak) and PIPKIγ staining (either strong or weak) was observed (P=0.00007) (See FIG. 13). The rare nuclear (n=8) E-cadherin staining pattern correlated with negative PIPKIγ staining (P=0.008). A stronger correlation was observed when comparing all cases with negative or inappropriately localized E-cadherin with negative PIPKIγ staining (P=0.000001). In this regard, PIPKIγ staining was comparable with other breast cancer biomarkers (FIG. 13).

FIG. 12B shows representative breast carcinomas from different patients that stain either negative, weakly positive or strongly positive for PIPKI γ (left, middle and right panels, respectively).

HER-1 expression and PIPKIγ expression were also evaluated. Overexpression of HER1 has been linked to increased metastasis of cancerous cells and poor prognosis of breast cancer. In tumor tissue sections, strong HER1 expression correlated with strong PIPKIγ staining, while weak HER1 expression correlated with greatly reduced PIPKIγ expression (FIG. 12C, FIG. 13). Since HER1 expression is correlated to PIPKIγ expression in breast cancer cells, this suggests that HER1 and PIPKIγ may cooperate to facilitate breast cancer metastasis.

Figure 11:
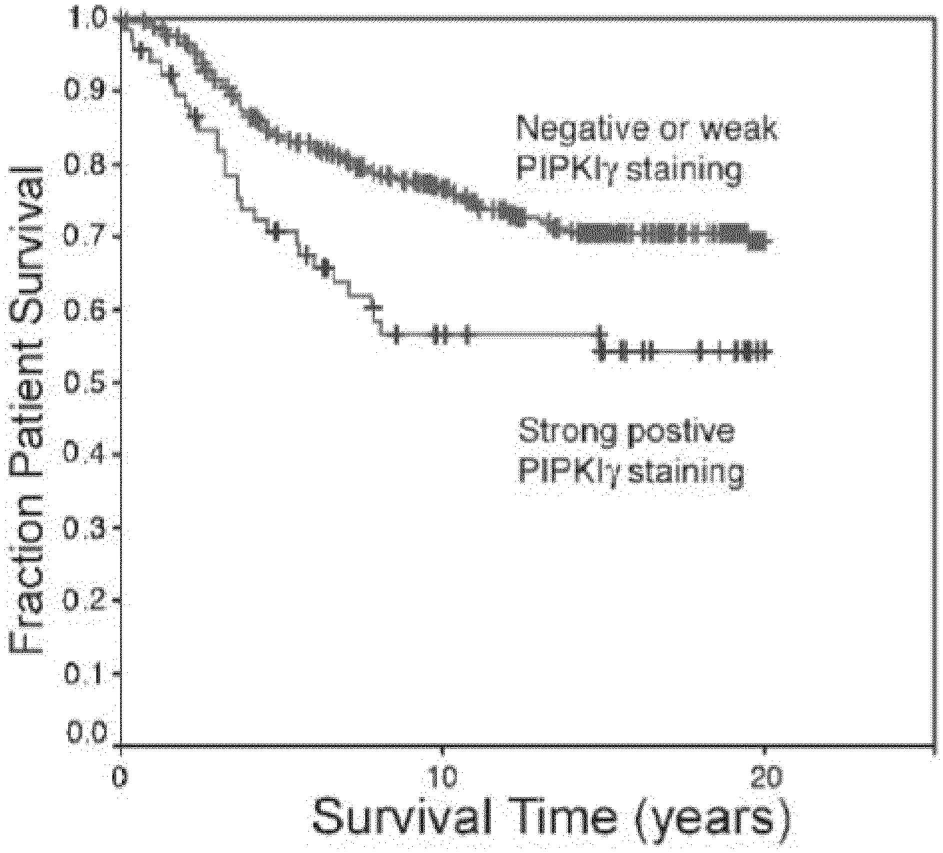
FIG. 11 shows a Kaplan Meier Survival plot (survival time vs. fraction patient survival) in breast cancer tissue samples tested for PIPKIγ expression.

PIPKIγ expression correlates to breast cancer prognosis (FIG. 11). Using a tissue microarray constructed out of 438 archival invasive breast carcinoma samples, Kaplan-Meier survival curves were generated for PIPKIγ expression. As shown in FIG. 11, these curves show that strong positive PIPKIγ expression was correlated to worse patient outcome. As the expression of PIPKIγ is inversely correlated to the survival of breast cancer patients, this indicates the prognostic value of PIPKIγ in breast cancer cases.

F. Assays to Screen for Agents which Modulate PIPKIγ 700 or 707 Activity

The following exemplary screening assays may be used to identify agents which modulate the activity of PIPKIγ 700 or 707 (e.g., either enhance or inhibit PIPKIγ 700 or 707 activity or alter PIPKIγ 700 or 707 localization). Such agents may include, but are not limited to proteins (including antibodies), nucleic acids, and organic and inorganic chemical compounds and salts thereof. Such agents may modulate PIPKIγ 700 or 707 directly (e.g., the agent may bind to the protein) or indirectly (e.g., the agent may act on another protein which interacts with the splice variant, such as SNX5 or LMO4). Agents which modulate the activity of PIPKIγ 700 or 707 may be useful as therapeutics to treat conditions in which aberrant PIPKIγ 700 or 707 activity (e.g., due to aberrant expression or localization of the splice variant) may influence a disease, symptom or condition such as, for example, longevity in breast cancer patients.

PIPKIγ 707 activity may include, for example, lipid kinase activity and/or SNX5 and/or b-catenin binding activity. Similarly, PIPPKIγ 700 activity may include lipid kinase activity and/or LMO4 and/or b-catenin binding activity.

In a screening assay to identify agents which modulate kinase activity, methods such as described above in Ling, et al. (2002) Nature 420:89-93 may be employed. Briefly, conditions for a kinase reaction are established and may include ATP (e.g., with a labeled terminal phosphate group), a substrate to be phosphorylated, (e.g., phosphatidylinositol 4-phosphate, "PI4P"), and appropriate buffers. The PIPKIγ splice variant can then be added to the test reaction in the presence or absence of the test agent. An increase or decrease in kinase activity in the reaction containing the test agent can then be determined, as compared to, for example, a reaction under the same conditions without the test agent. As described above, the kinase activity of PIPKIγ 707 protein appears necessary for appropriate localization. Thus, an agent which can alter this activity may prove important in modulating cellular functions which depend on PIPKIγ 707 activity and its appropriate localization. Moreover, an agent which alters lipid kinase activity of either protein will also alter $PI4,5P_2$ levels generated by that protein. Again, such an alteration may effect particular biochemical pathways and cellular functions.

Formats for screening assays to identify agents which modulate the binding of PIPKIγ 700 or 707 to other proteins, such as β-catenin, LMO4 or SNX5 respectively, are also well known in the art, and may include but are not limited to immunoprecipitations, two-hybrid screens, gel-shift analyses, and GST-pull down approaches. Such methods involve the detection and measurement of the binding interaction of the "target" proteins (e.g., PIPKIγ 707 and SNX5) in the presence and absence of the test agent.

When assaying test agents, a control may also be included. Controls may be known agents, which have a high affinity for binding and inhibiting or enhancing the interaction between the target proteins, or a low affinity for binding and inhibiting or enhancing the interaction between the target protein. Similarly, control agents may be those know to inhibit or enhance PIPKIγ 700 or 707 kinase activity.

An agent which modulates the activity of PIPKIγ 700 or 707 may also include agents which modulate the expression of PIPKIγ 700 or 707. For example, the expression of PIPKIγ 700 or 707 may be inhibited using inhibitory RNAs such as ribozymes, antisense RNA, RNAi, siRNA and the like. These RNA molecules may be designed to specifically interact with the nucleic acid sequences encoding PIPKIγ 700 or 707 to decrease the expression of PIPKIγ 700 or 707 thereby decreasing activity (e.g., kinase activity and binding to SNX5 or LMO4 and/or β-catenin). Because the RNA molecules encoding PIPKIγ 700 or 707 are alternatively spliced and are unique from other PIPKIγ RNA molecules, inhibitory RNA molecules may be directed to these unique sequences. For example, both PIPKIγ 700 and 707 include exon 16c, while only the PIPKIγ 700 variant includes exon 16b. Thus, inhibitory nucleic acid molecules may include sequences directed to these unique regions.

An agent which modulates the localization of PIPKIγ 700 or PIPKIγ 707 may also modulate the activity of the protein. Accordingly, assays which test for changes in intracellular localization of a PIPKIγ protein in the presence and absence of a test agent are also embodied herein. Such assays are well known in the art and include but are not limited to hybridization assays with labeled antibodies.

G. Prognostic Methods

In some embodiments, the PIPKIγ 668, 700 and 707 polynucleotides and proteins are used to develop prognostic evaluation methods for patients suspected of acquiring an oncogenic disorder such as breast cancer. For example, biological samples obtained from patients are assayed for the presence, amount or localization of the PIPKIγ 668, 700 and 707 polynucleotides (e.g., mRNA) or the proteins themselves. If such a nucleic acid or protein is present in normal tissue, and the development of the oncogenic disorder is affected by or characterized by an abnormal quantity or localization of the protein or nucleic acid, the assay compares the quantity and/or localization in the biological sample to the range expected in normal, non-oncogenic tissue of the same cell type.

For example, in some cancers, one or more of the PIPKIγ 640, 668, 700 or 707 proteins is present at an abnormal level, abnormally localized, or is in a modified form relative to the level, localization or form expressed in normal, non-oncogenic tissue of the same cell type. For example, as shown in FIG. 11, some breast cancer tissue samples exhibit higher levels of PIPKIγ. As shown in FIG. 11, patients with such levels of PIPKIγ exhibit a poor prognosis with respect to longevity.

In some embodiments, overexpression of PIPKIγ 700 or 707 indicates a particularly aggressive course of cancer. Thus, an assessment of the PIPKIγ 700 or 707 levels of mRNA and/or protein in breast cancer tissue cells provides valuable clues as to the course of action to be undertaken in treatment of such an oncogenic disorder. Assays of this type are well known to those of skill in the art, and include, but are not limited to, Northern blot analysis, RNAse protection assays, and PCR for determining mRNA levels. Additionally, mRNA hybridization assays may be performed on fixed tissue samples to determine mRNA localization and amount. Assays to determine PIPKIγ 700 or 707 protein levels are also well known to those of skill in the art, and may include, but are not limited to, Western blot analysis, immunoprecipitation, and ELISA analysis. Additionally, hybridization assays with labeled antibodies may be performed on tissue samples to determine protein localization and relative amount.

Further, in some embodiments, such assays are also performed using cancer markers, such as HER1, HER2 and LMO4. For example, in some embodiments, high HER1 or HER2 levels in conjunction with low PIPKIγ levels in oncogenic tissue correlate with a better prognosis (e.g., greater longevity) than high HER1 or HER2 levels and a normal to high level of PIPKIγ expression in oncogenic tissue (e.g., breast carcinoma tissue, see e.g., FIG. 12, FIG. 13).

H. Pharmaceutical Compositions and Therapies

An effective amount of an agent which modulates the activity of PIPKIγ 700 or PIPKIγ 707 is an amount which prevents, eliminates or alleviates at least one sign or symptom of a condition, disorder or disease involving PIPKIγ 700 or PIPKIγ 707. Such a condition, disorder or disease may include an oncogenic condition, such as breast cancer. Signs or symptoms associated with such conditions may be monitored to determine the effectiveness of the therapeutic agent. By way of example but not by way of limitation, such signs and symptoms may include the spread of the cancer, tumor size, weakness, fatigue and pain. The specific amount of the agent required to achieve the desired outcome of preventing, eliminating or alleviating a sign or symptom of such a condition or disease will be dependent on the pharmaceutical composition of the agent, the patient, the condition of the patient, the method of administration, and the condition or disease being prevented or treated.

Some embodiments include an agent which modulates the activity of PIPKIγ 700 or PIPKIγ 707 (e.g., increases, decreases or alters protein localization) and which may be attached to a targeting moiety to deliver the agent to a cell-type or tissue of interest. This could potentially decrease harmful side-effects of modulating the activity of PIPKIγ 700 and PIPKIγ 707 in all cell-types or tissues.

Gene therapy techniques are also embodied herein. For example, target cell populations may be modified by introducing wild-type or altered forms of PIPKIγ 700 or PIPKIγ 707 to modulate the levels and localization of $PI4,5P_2$ and/or the activity and localization of other proteins such as SNX5 and LMO4. Altered forms of the splice variant proteins may include deletion or missense mutants that retain the ability to interact with other components of a particular signaling pathway but that cannot otherwise function in signal transduction. Such mutants may be used to inhibit an abnormal, deleterious signal transduction event. In yet another embodiment, a therapy or therapeutic method may include moderate overexpression of PIPKIγ 700 and/or PIPKIγ 707; such overexpression may have therapeutic value in treating or preventing some oncogenic diseases or disorders associated with aberrant PIPKIγ expression and/or localization.

I. Kits

Any of the above described nucleic acids, antibodies, prognostic compositions, or pharmaceutical compositions may be provided in kit form. For example, kits for making a prognosis regarding an oncogenic condition may include one or more of the following: 1) an antibody which specifically binds to one or more of PIPKIγ 700, PIPKIγ 707, a fragment or variant thereof; 2) one or more nucleic acids capable of hybridizing to PIPKIγ 700 nucleic acid, PIPKIγ 707 nucleic acid, a fragment or variant thereof; 3) a polypeptide comprising PIPKIγ 700, PIPKIγ 707, a fragment or a variant thereof; 4) control reagents; 5) instructions for carrying out the test procedure, troubleshooting and for interpreting results. Such a kit may be coupled with a therapeutic compositions in the event that the assay results indicate such a treatment is necessary.

What is claimed is:

1. An isolated polynucleotide encoding a polypeptide having lipid kinase activity, wherein the polynucleotide comprises a sequence selected from the group consisting of:

a) a cDNA sequence encoding an amino acid sequence having at least about 95% sequence identity to SEQ ID NO: 4;

b) a polynucleotide sequence comprising SEQ ID NO: 2;

c) a polynucleotide sequence which is fully complementary to the sequence of (a) or (b).

2. An expression vector comprising the polynucleotide of claim 1.

3. An isolated host cell comprising the expression vector of claim 2.

4. A method of producing a polypeptide encoded by a polynucleotide selected from the group consisting of the polynucleotide of claim 1, the method comprising:

culturing a cell under conditions suitable for expression of the polypeptide, wherein the cell is transformed with the polynucleotide, and wherein the polynucleotide comprises a promoter sequence operably linked to the polynucleotide.

5. A kit comprising the nucleic acid of claim 1.

* * * * *